US009675286B2

(12) United States Patent
Diab

(10) Patent No.: US 9,675,286 B2
(45) Date of Patent: Jun. 13, 2017

(54) PLETHYSMOGRAPH PULSE RECOGNITION PROCESSOR

(75) Inventor: Mohamed K. Diab, Ladera Ranch, CA (US)

(73) Assignee: Masimo Corporation, Irvine, CA (US)

( * ) Notice: Subject to any disclaimer, the term of this patent is extended or adjusted under 35 U.S.C. 154(b) by 1119 days.

(21) Appl. No.: 13/196,220

(22) Filed: Aug. 2, 2011

(65) Prior Publication Data

US 2011/0288383 A1 Nov. 24, 2011

Related U.S. Application Data

(63) Continuation of application No. 11/418,328, filed on May 3, 2006, now Pat. No. 7,988,637, which is a continuation of application No. 10/974,095, filed on Oct. 27, 2004, now Pat. No. 7,044,918, which is a continuation of application No. 10/267,446, filed on Oct. 8, 2002, now Pat. No. 6,816,741, which is a continuation of application No. 09/471,510, filed on Dec. 23, 1999, now Pat. No. 6,463,311.

(60) Provisional application No. 60/114,127, filed on Dec. 30, 1998.

(51) Int. Cl.
 *A61B 5/00* (2006.01)
 *A61B 5/021* (2006.01)
 *A61B 5/1455* (2006.01)
 *A61B 5/024* (2006.01)

(52) U.S. Cl.
 CPC ...... *A61B 5/14551* (2013.01); *A61B 5/02416* (2013.01); *A61B 5/7264* (2013.01)

(58) Field of Classification Search
 USPC ........................................ 600/301, 500, 323
 See application file for complete search history.

(56) References Cited

U.S. PATENT DOCUMENTS

| | | | |
|---|---|---|---|
| 4,051,522 A | 9/1977 | Healy | |
| 4,085,378 A | 4/1978 | Ryan | |
| 4,295,471 A | 10/1981 | Kaspari | |
| 4,623,248 A | 11/1986 | Sperinde | |
| 4,653,498 A | 3/1987 | New | |
| 4,745,398 A | 5/1988 | Abel | |
| 4,765,340 A | 8/1988 | Sakai | |
| 4,800,495 A | 1/1989 | Smith | |
| 4,802,486 A * | 2/1989 | Goodman et al. ............ 600/324 |
| 4,824,242 A * | 4/1989 | Frick .................. A61B 5/14551 |
| | | | 356/41 |
| 4,846,183 A * | 7/1989 | Martin ........................ 600/336 |
| 4,863,265 A | 9/1989 | Flower | |

(Continued)

FOREIGN PATENT DOCUMENTS

DE 3328862 A1 2/1985
EP 0 104 771 A2 4/1984

(Continued)

OTHER PUBLICATIONS

US 8,845,543, 09/2014, Diab et al. (withdrawn)

(Continued)

*Primary Examiner* — Michael Kahelin
*Assistant Examiner* — Mitchell E Alter
(74) *Attorney, Agent, or Firm* — Knobbe, Martens, Olson & Bear, LLP

(57) ABSTRACT

A time domain rule-based processor provides recognition of pulses in a pulse oximeter-derived waveform.

4 Claims, 19 Drawing Sheets

(56) References Cited

U.S. PATENT DOCUMENTS

| | | | |
|---|---|---|---|
| 4,870,588 A | 9/1989 | Merhav | |
| 4,911,167 A | 3/1990 | Corenman | |
| 4,934,372 A | 6/1990 | Corenman et al. | |
| 4,938,228 A | 7/1990 | Righter et al. | |
| 4,942,877 A | 7/1990 | Sakai | |
| 4,955,379 A | 9/1990 | Hall | |
| 4,960,126 A | 10/1990 | Conlon et al. | |
| 4,960,128 A | 10/1990 | Gordon et al. | |
| 4,964,408 A | 10/1990 | Hink et al. | |
| 4,965,840 A | 10/1990 | Subbarao | |
| 5,003,252 A | 3/1991 | Nystrom | |
| RE33,643 E | 7/1991 | Isaacson et al. | |
| 5,041,187 A | 8/1991 | Hink et al. | |
| 5,069,213 A | 12/1991 | Polczynski | |
| 5,163,438 A | 11/1992 | Gordon et al. | |
| 5,170,791 A | 12/1992 | Boos et al. | |
| 5,188,108 A | 2/1993 | Secker | |
| 5,190,038 A | 3/1993 | Polson | |
| 5,193,124 A | 3/1993 | Subbarao | |
| 5,218,962 A | 6/1993 | Mannheimer | |
| 5,226,417 A | 7/1993 | Swedlow | |
| 5,243,992 A | 9/1993 | Eckerle et al. | |
| 5,246,002 A | 9/1993 | Prosser | |
| 5,259,381 A | 11/1993 | Cheung | |
| 5,270,942 A | 12/1993 | Reed | |
| 5,274,548 A | 12/1993 | Bernard et al. | |
| 5,299,120 A | 3/1994 | Kaestle | |
| 5,307,284 A | 4/1994 | Brunfeldt | |
| 5,319,355 A | 6/1994 | Russek | |
| 5,331,394 A | 7/1994 | Shalon et al. | |
| 5,337,744 A | 8/1994 | Branigan | |
| 5,341,805 A | 8/1994 | Stavridi et al. | |
| 5,345,510 A | 9/1994 | Singhi | |
| 5,349,519 A | 9/1994 | Kaestle | |
| 5,353,356 A | 10/1994 | Waugh et al. | |
| 5,355,882 A | 10/1994 | Ukawa | |
| 5,357,965 A | 10/1994 | Hall et al. | |
| 5,365,934 A | 11/1994 | Leon et al. | |
| 5,368,224 A | 11/1994 | Richardson | |
| D353,195 S | 12/1994 | Savage et al. | |
| D353,196 S | 12/1994 | Savage et al. | |
| 5,377,676 A | 1/1995 | Vari et al. | |
| 5,384,451 A | 1/1995 | Smith et al. | |
| 5,398,003 A | 3/1995 | Heyl et al. | |
| 5,404,003 A | 4/1995 | Smith | |
| 5,406,952 A | 4/1995 | Barnes | |
| D359,546 S | 6/1995 | Savage et al. | |
| 5,421,329 A | 6/1995 | Casciani | |
| 5,431,170 A | 7/1995 | Mathews | |
| D361,840 S | 8/1995 | Savage et al. | |
| 5,438,983 A | 8/1995 | Falcone | |
| 5,442,940 A | 8/1995 | Secker | |
| D362,063 S | 9/1995 | Savage et al. | |
| 5,448,991 A | 9/1995 | Polson | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,481,620 A | 1/1996 | Vaidyanathan | |
| 5,482,036 A | 1/1996 | Diab et al. | |
| 5,490,505 A | 2/1996 | Diab et al. | |
| 5,494,043 A | 2/1996 | O'Sullivan et al. | |
| 5,503,148 A | 4/1996 | Pologe | |
| 5,533,511 A | 7/1996 | Kaspari et al. | |
| 5,534,851 A | 7/1996 | Russek | |
| 5,535,753 A | 7/1996 | Petrucelli et al. | |
| 5,542,421 A | 8/1996 | Erdman | |
| 5,549,111 A | 8/1996 | Wright et al. | |
| 5,553,615 A | 9/1996 | Carim et al. | |
| 5,561,275 A | 10/1996 | Savage et al. | |
| 5,562,002 A | 10/1996 | Lalin | |
| 5,575,284 A | 11/1996 | Athan | |
| 5,588,435 A | 12/1996 | Weng et al. | |
| 5,590,649 A | 1/1997 | Caro et al. | |
| 5,602,924 A | 2/1997 | Durand et al. | |
| 5,608,820 A | 3/1997 | Vaidyanathan | |
| 5,610,996 A | 3/1997 | Eller | |
| 5,623,937 A | 4/1997 | Sasaki | |
| 5,632,272 A | 5/1997 | Diab et al. | |
| 5,638,816 A | 6/1997 | Kiani-Azarbayjany et al. | |
| 5,638,818 A * | 6/1997 | Diab et al. | 600/476 |
| 5,645,440 A | 7/1997 | Tobler et al. | |
| 5,647,369 A | 7/1997 | Petrucelli et al. | |
| 5,651,370 A | 7/1997 | Hersh et al. | |
| 5,652,566 A | 7/1997 | Lambert | |
| 5,682,898 A * | 11/1997 | Aung et al. | 600/484 |
| 5,685,299 A | 11/1997 | Diab et al. | |
| 5,720,293 A | 2/1998 | Quinn | |
| D393,830 S | 4/1998 | Tobler et al. | |
| 5,738,104 A | 4/1998 | Lo et al. | |
| 5,743,262 A | 4/1998 | Lepper | |
| 5,755,226 A | 5/1998 | Carim et al. | |
| 5,758,644 A | 6/1998 | Diab et al. | |
| 5,760,910 A | 6/1998 | Lepper, Jr. et al. | |
| 5,766,127 A | 6/1998 | Pologe et al. | |
| 5,769,785 A | 6/1998 | Diab et al. | |
| 5,782,237 A | 7/1998 | Casciani | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,820,267 A | 10/1998 | Nobles | |
| 5,823,950 A | 10/1998 | Diab et al. | |
| 5,830,131 A | 11/1998 | Caro et al. | |
| 5,833,618 A | 11/1998 | Caro et al. | |
| 5,842,979 A | 12/1998 | Jarman | |
| 5,853,364 A * | 12/1998 | Baker et al. | 600/300 |
| 5,860,919 A | 1/1999 | Kiani-Azarbayjany et al. | |
| 5,865,736 A | 2/1999 | Baker, Jr. et al. | |
| 5,890,929 A | 4/1999 | Mills et al. | |
| 5,891,023 A | 4/1999 | Lynn | |
| 5,904,654 A | 5/1999 | Wohltmann et al. | |
| 5,919,134 A | 7/1999 | Diab | |
| 5,921,921 A | 7/1999 | Potratz et al. | |
| 5,924,980 A * | 7/1999 | Coetzee | A61B 5/14551 128/901 |
| 5,934,925 A | 8/1999 | Tobler et al. | |
| 5,940,182 A | 8/1999 | Lepper, Jr. et al. | |
| 5,950,139 A | 9/1999 | Korycan | |
| 5,987,343 A | 11/1999 | Kinast | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,047,203 A | 4/2000 | Sackner et al. | |
| 6,064,910 A | 5/2000 | Andersson et al. | |
| 6,067,462 A | 5/2000 | Diab et al. | |
| 6,081,735 A | 6/2000 | Diab et al. | |
| 6,083,172 A | 7/2000 | Baker, Jr. et al. | |
| 6,088,607 A | 7/2000 | Diab et al. | |
| 6,101,410 A | 8/2000 | Panescu et al. | |
| 6,110,522 A | 8/2000 | Lepper, Jr. et al. | |
| 6,119,026 A | 9/2000 | McNulty et al. | |
| 6,122,535 A | 9/2000 | Kaestle et al. | |
| 6,124,597 A | 9/2000 | Shehada | |
| 6,128,521 A | 10/2000 | Marro et al. | |
| 6,129,675 A | 10/2000 | Jay | |
| 6,135,952 A | 10/2000 | Coetzee | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,188,407 B1 | 2/2001 | Smith et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |

(56) References Cited

U.S. PATENT DOCUMENTS

| | | |
|---|---|---|
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,312,387 B1 | 11/2001 | Nissila et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,393,311 B1 | 5/2002 | Edgar, Jr. et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,575,915 B2 | 6/2003 | Nissila et al. |
| 6,580,086 B1 | 6/2003 | Schulz et al. |
| 6,584,336 B1 | 6/2003 | Al Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| 7,225,013 B2 | 5/2007 | Geva et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |

(56) References Cited

U.S. PATENT DOCUMENTS

| | | |
|---|---|---|
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al-Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |

(56) References Cited

U.S. PATENT DOCUMENTS

| | | |
|---|---|---|
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 2002/0082488 A1 | 6/2002 | Al-Ali |
| 2002/0161291 A1 | 10/2002 | Kiani |
| 2003/0000522 A1 | 1/2003 | Lynn |
| 2003/0018241 A1 | 1/2003 | Mannheimer |
| 2003/0073890 A1 | 4/2003 | Hanna |
| 2003/0120164 A1 | 6/2003 | Nielsen |
| 2009/0247984 A1 | 10/2009 | Lamego et al. |
| 2009/0275844 A1 | 11/2009 | Al-Ali |

(56) References Cited

U.S. PATENT DOCUMENTS

| | | |
|---|---|---|
| 2010/0004518 A1 | 1/2010 | Vo et al. |
| 2010/0030040 A1 | 2/2010 | Poeze et al. |
| 2010/0261979 A1 | 10/2010 | Kiani |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |

FOREIGN PATENT DOCUMENTS

| | | |
|---|---|---|
| EP | 0 352 923 A1 | 1/1990 |
| EP | 0 645 117 A1 | 3/1995 |
| EP | 0 659 384 A1 | 6/1995 |
| WO | WO 84/03032 | 8/1984 |
| WO | WO 92/11803 | 7/1992 |
| WO | WO 92/15955 | 9/1992 |
| WO | WO 92/20273 | 11/1992 |
| WO | WO 95/21567 | 8/1995 |
| WO | WO 98/43071 | 10/1998 |

OTHER PUBLICATIONS

U.S. Appl. No. 90/012,403, filed Jul. 23, 2012, requesting ex parte reexamination of U.S. Pat. No. 6,263,222, including accompanying Reexam Request, claim charts, and other documentation filed under 37 C.F.R. § 1.510 and 35 U.S.C. § 302.

U.S. Appl. No. 90/012,409, filed Aug. 17, 2012, requesting ex parte reexamination of U.S. Pat. No. 6,699,194, including accompanying Reexam Request, claim charts, and other documentation filed under 37 C.F.R. § 1.510 and 35 U.S.C. § 302.

(56) References Cited

OTHER PUBLICATIONS

U.S. Appl. No. 90/012,463, filed Sep. 5, 2012, requesting ex parte reexamination of of U.S. Pat. No. 7,215,984, including accompanying Reexam Request, claim charts, and other documentation filed under 37 C.F.R. § 1.510 and 35 U.S.C. § 302.
U.S. Appl. No. 90/012,532, filed Sep. 13, 2012, requesting ex parte reexamination of U.S. Pat. No. 7,499,835, including accompanying Reexam Request, claim charts, and other documentation filed under 37 C.F.R. § 1.510 and 35 U.S.C. § 302.
U.S. Appl. No. 90/012,534, filed Sep. 13, 2012, requesting ex parte reexamination of U.S. Pat. No. 7,962,188, including accompanying Reexam Request, claim charts, and other documentation filed under 37 C.F.R. § 1.510 and 35 U.S.C. § 302.
U.S. Appl. No. 90/012,538, filed Sep. 13, 2012, requesting ex parte reexamination of U.S. Pat. No. 7,377,899, including accompanying Reexam Request, claim charts, and other documentation filed under 37 C.F.R. § 1.510 and 35 U.S.C. § 302.
U.S. Appl. No. 90/012,541, filed Sep. 13, 2012, requesting ex parte reexamination of U.S. Pat. No. 7,899,507, including accompanying Reexam Request, claim charts, and other documentation filed under 37 C.F.R. § 1.510 and 35 U.S.C. § 302.
U.S. Appl. No. 90/012,542, filed Sep. 13, 2012, requesting ex parte reexamination of U.S. Pat. No. 8,180,420, including accompanying Reexam Request, claim charts, and other documentation filed under 37 C.F.R. § 1.510 and 35 U.S.C. § 302.
U.S. Appl. No. 90/012,543, filed Sep. 13, 2012, requesting ex parte reexamination of U.S. Pat. No. 6,850,787, including accompanying Reexam Request, claim charts, and other documentation filed under 37 C.F.R. § 1.510 and 35 U.S.C. § 302.
U.S. Appl. No. 90/012,546, filed Sep. 13, 2012, requesting ex parte reexamination of U.S. Pat. No. 7,438,683, including accompanying Reexam Request, claim charts, and other documentation filed under 37 C.F.R. § 1.510 and 35 U.S.C. § 302.
U.S. Appl. No. 90/012,548, filed Sep. 13, 2012, requesting ex parte reexamination of U.S. Pat. No. 7,880,606, including accompanying Reexam Request, claim charts, and other documentation filed under 37 C.F.R. § 1.510 and 35 U.S.C. § 302.
U.S. Appl. No. 90/012,551, filed Sep. 13, 2012, requesting ex parte reexamination of U.S. Pat. No. 6,970,792, including accompanying Reexam Request, claim charts, and other documentation filed under 37 C.F.R. § 1.510 and 35 U.S.C. § 302.
U.S. Appl. No. 90/012,553, filed Sep. 13, 2012, requesting ex parte reexamination of U.S. Pat. No. 7,024,233, including accompanying Reexam Request, claim charts, and other documentation filed under 37 C.F.R. § 1.510 and 35 U.S.C. § 302.
U.S. Appl. No. 90/012,555, filed Sep. 13, 2012, requesting ex parte reexamination of U.S. Pat. No. 7,440,787, including accompanying Reexam Request, claim charts, and other documentation filed under 37 C.F.R. § 1.510 and 35 U.S.C. § 302.
U.S. Appl. No. 90/012,557, filed Sep. 13, 2012, requesting ex parte reexamination of U.S. Pat. No. 8,150,487, including accompanying Reexam Request, claim charts, and other documentation filed under 37 C.F.R. § 1.510 and 35 U.S.C. § 302.
U.S. Appl. No. 90/012,559, filed Sep. 13, 2012, requesting ex parte reexamination of U.S. Pat. No. 8,190,223, including accompanying Reexam Request, claim charts, and other documentation filed under 37 C.F.R. § 1.510 and 35 U.S.C. § 302.
U.S. Appl. No. 90/012,561, filed Sep. 14, 2012, requesting ex parte reexamination of U.S. Pat. No. 8,019,400, including accompanying Reexam Request, claim charts, and other documentation filed under 37 C.F.R. § 1.510 and 35 U.S.C. § 302.
U.S. Appl. No. 90/012,566, filed Sep. 14, 2012, requesting ex parte reexamination of U.S. Pat. No. 7,530,955, including accompanying Reexam Request, claim charts, and other documentation filed under 37 C.F.R. § 1.510 and 35 U.S.C. § 302.
U.S. Appl. No. 90/012,567, filed Sep. 14, 2012, requesting ex parte reexamination of U.S. Pat. No. 6,684,090, including accompanying Reexam Request, claim charts, and other documentation filed under 37 C.F.R. § 1.510 and 35 U.S.C. § 302.
U.S. Appl. No. 90/012,568, filed Sep. 14, 2012, requesting ex parte reexamination of U.S. Pat. No. 8,128,572, including accompanying Reexam Request, claim charts, and other documentation filed under 37 C.F.R. § 1.510 and 35 U.S.C. § 302.
U.S. Appl. No. 90/012,699, filed Oct. 4, 2012, requesting ex parte reexamination of U.S. Pat. No. 6,002,952, including accompanying Reexam Request, claim charts, and other documentation filed under 37 C.F.R. § 1.510 and 35 U.S.C. § 302.
U.S. Appl. No. 90/002,183, filed Sep. 12, 2012, requesting inter parte reexamination of U.S. Pat. No. 7,530,955, including accompanying Reexam Request, claim charts, and other documentation filed under 37 C.F.R. § 1.913 and 35 U.S.C. § 311.
Blitt, Casey D., *Monitoring in Anesthesia and Critical Care Medicine*, (2d ed. 1990).
Boualem Boashah, *Estimating and Interpreting the Instantaneous Frequency of a Signal—Part I: Fundamentals*, Proceedings of the IEEE, vol. 80, No. 4 (Apr. 1992).
Boualem Boashash, *Note on the Use of the aligner Distribution for Time-Frequency Signal Analysis*, IEEE Transactions on Acoustics, Speech, and Signal Processing, vol. 36, No. 9 (Sep. 1988).
Business Wire, "Mallinckrodt Announces the Nellcor N-395 Pulse Oximeter with Oxismart XL and SatSeconds," Oct. 7, 1999.
Edward Bedrosian, *The Analytic Signal Representation of Modulating Waveforms* (1962).
Hanzo et al., "A Portable Multimedia Communicator Scheme", *Multimedia Technologies and Future Applications: Proceedings of the IEEE International Symposium* (1994).
Maciej Niedzwiecki et al., "Smoothing of Discontinuous Signals: The Competitive Approach" *IEEE Transactions on Signal Processing*, vol. 43, No. 1, Jan. 1995, pp. 1-13.
Steven W. Smith, *The Scientist and Engineer's Guide to Digital Signal Processing*, § 8 ($1^{st}$ ed. 1997).
Declaration of Perry D. Oldham in Support of Masimo Opposition to Defendant's Motion for Summary Judgment of Invalidity and Noninfringement of U.S. Pat. No. 7,215,984, vol. 1, Doc. 556, *Masimo Corporation v. Philips Electronics North America Corporation and Philips Medizin Systeme Böblingen GHBH*, (District of Delaware, Case No. 1:09-cv-00080 (LPS/MPT) dated Sep. 28, 2012. (Redacted).
Declaration of Perry D. Oldham in Support of Masimo's Opposition to Defendant's Motion for Summary Judgment of Invalidity and Noninfringement of U.S. Pat. No. 7,215,984, vol. 2, Doc. 558, *Masimo Corporation v. Philips Electronics North American Corporation and Philips Medizin Systeme Böblingen GMBH*, (District of Delaware, Case No. 1:09-cv-00080 (LPS/MPT) dated Sep. 28, 2012. (Redacted).
Masimo Corporation's Answering Brief in Opposition to Defendant's Motion for Summary Judgment of Invalidity and Noninfringement of U.S. Pat. No. 7,215,984, Doc. 555, *Masimo Corporation v. Philips Electronics North America Corporation and Philips Medizin Systeme Böblingen GHBH*, (District of Delaware, Case No. 1:09-cv-00080 (LPS/MPT) dated Sep. 28, 2012. (Redacted).
Philip's Opening Brief in Support of Defendant's Motion for Summary Judgment of Invalidity and Noninfringement of U.S. Pat. No. 7,215,984, Doc. 442, *Masimo Corporation v. Philips Electronics North America Corporation and Philips Medizin Systeme Böblingen GHBH*, District of Delaware, Case No. 1:09-cv-00080 (LPS/MPT) dated Aug. 21, 2012. (Redacted).
Philip Defendant's Motion for Summary Judgment of Invalidity and Noninfringement of U.S. Pat. No. 7,215,984, Doc. 394, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Reply Brief in Support of Defendants' Motion for Summary Judgment of Invalidity and Noninfringement of U.S. Pat. No. 7,216,984, Doc. 609, *Masimo Corporation V. Philips Electronics North America Corporation and Philips Medizin Systeme Böblingen GHBH*, (District of Delaware, Case No. 1:09-cv-00080 (LPS/MPT) dated Oct. 26, 2012. (Redacted).
Declaration of Gail Baura, Ph.D. in Support of Masimo's Opposition to Defendant's Motion for Summary Judgment of Invalidity of U.S. Pat. No. 7,215,984, Doc. 561, *Masimo Corporation v. Philips*

(56) References Cited

OTHER PUBLICATIONS

*Electronics North American Corporation and Philips Medizin System Böblingen GMBH*, (District of Delaware, Case No. 1:09-cv-00080 (LPS/MPT) dated Sep. 28, 2012. (Redacted).

Declaration of Gail Baura, Ph.D. in Support of Masimo's Opposition to Defendant's Motion for Summary Judgment of Invalidity of U.S. Pat. No. 5,632,272, Doc. 554, *Masimo Corporation v. Philips Electronics North America Corporation and Philips Medizin Systeme Böblingen GMBH*, (District of Delaware, Case No. 1:09-cv-00080 (LPS/MPT) dated Aug. 28, 2012. (Redacted).

Declaration of Perry D. Oldham in Support of Masimo Opposition to Defendant's Motion for Summary Judgment of Invalidity of U.S. Pat. No. 5,632,272, Doc. 553, *Masimo Corporation v. Philips Electronics North America Corporation and Philips Medizin Systeme Böblingen GHBH*, (District of Delaware, Case No. 1:09-cv-00080 (LPS/MPT) dated Sep. 28, 2012. (Redacted).

Masimo Corporation's Answering Brief in Opposition to Defendant's Motion for Summary Judgment of Invalidity and Noninfringement of U.S. Pat. No. 5,632,272, Doc. 552, *Masimo Corporation v. Philips Electronics North America Corporation and Philips Medizin System Böblingen GMBH*, (District of Delaware, Case No. 1:09-cv-00080 (LPS/MPT) dated Sep. 28, 2012. (Redacted).

Opening Brief in Support of Defendants' Motion for Summary Judgment of Invalidity and Noninfringement of U.S. Pat. No. 5,632,272, Doc. 444, *Masimo Corporation v. Philips Electronics North America Corporation and Philips Medizin Systeme Böblingen GMBH*, (District of Delaware, Case No. 1:09-cv-00080 (LPS/MPT) dated Aug. 21, 2012. (Redacted).

Defendant's Motion for Summary Judgment of Invalidity and Noninfringement of U.S. Pat. No. 5,632,272, Doc. 402, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.

Reply Brief in Support of Defendant's Motion for Summary Judgment of Invalidity and Noninfringement of U.S. Pat. No. 5,632,272, Doc. 614, *Masimo Corporation v. Philips Electronics North America Corporation and Philips Medizin Systeme Böblingen GMBH*, (District of Delaware, Case No. 1:09-cv-00080 (LPS/MPT) dated Oct. 26, 2012 (Redacted).

Declaration of Mohammed K. Diab in Support of Masimo's Opposition to Defendant's Motions for Summary Judgment of Invalidity and Noninfringement of U.S. Pat. No. 5,632,272 and 7,215,984, Doc. 563, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).

Declaration of Perry D. Oldham in Support of Masimo's Opposition to Defendant's Motion for Summary Judgment of Invalidity of U.S. Pat. No. 6,263,222, Doc. 550, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012 (Redacted).

Masimo Corporation's Answering Brief in Opposition to Defendant's Motion for Summary Judgment of Invalidity of U.S. Pat. No. 6,263,222, Doc. 549, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012 (Redacted).

Philips' Opening Brief in Support of Defendants' Motion for Summary Judgment of Invalidity of U.S. Pat. No. 6,263,222, Doc. 413, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.

Defendants' Motion for Summary Judgment of Invalidity of U.S. Pat. No. 6,263,222, Doc. 410, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.

Reply Brief in Support of Defendants' Motion for Summary Judgment of Invalidity of U.S. Pat. No. 6,263,222, Doc. 613, *Masimo Corporation v. Philips Electronics North America Corporation and Philips Medizin Systeme Böblingen GMBH*, (District of Delaware, Case No. 1:09-cv-00080 (LPS/MPT) dated Oct. 26, 2012 (Redacted).

Declaration of Gail Baura, Ph.D., in Support of Masimo's Opposition to Defendant's Motion for Summary Judgment of Invalidity of U.S. Pat. No. 6,263,222, Doc. 551, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).

V. Ya. Volkov, "Enhancing the Reliability and Accuracy of Pulse Oximetry with a Built-In Expert System," *Biomedical Engineering*, vol. 27, No. 3 (May-Jun. 1993) (translated from Russian).

Declaration of Gail Baura, Ph.D., in Support of Masimo's Opposition to Defendant's Motion for Summary Judgment of Invalidity of U.S. Pat. No. 6,699,194, Doc. 508, *Masimo Corporation v. Philips Electronics North America Corporation and Philips Medizin Systeme Böblingen GMBH*, (District of Delaware, Case No. 1:09-cv-00080 (LPS/MPT) dated Sep. 21, 2012.

Opening Brief in Support of Defendant's Motion for Summary Judgment of Invalidity of U.S. Pat. No. 6,689,194, Doc. 445, *Masimo Corporation v. Philips Electronics North America Corporation and Philips Medizin Systeme Böblingen GMBH*, (District of Delaware, Case No. 1:09-cv-0080 (LPS/MPT) dated Aug. 21, 2012. (Redacted).

Defendants' Motion for Summary Judgment of Invalidity of U.S. Pat. No. 6,699,194, Doc. 406, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.

Reply Brief in Support of Defendants' Motion for Summary Judgment of Invalidity of U.S. Pat. No. 6,699,194, Doc. 610, *Masimo Corporation v. Philips Electronics North America Corporation and Philips Medizin Systeme Böblingen GMBH*, (District of Delaware, Case No. 1:09-cv-00080 (LPS/MPT) dated Oct. 26, 2012. (Redacted).

Declaration of Perry D. Oldham in Support of Masimo Opposition to Defendant's Motion for Summary Judgment of Invalidity of U.S. Pat. No. 6,699,194, Doc. 548, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).

Scharf, "Optimization of Portable Pulse Oximetry Through Fourier Analysis".

Scharf, "Pulse Oximetry Through Spectral Analysis".

Rusch, "Master's Thesis," Graduate School University of South Florida, Tampa, Florida (Dec. 1994).

Philips' Response to Masimo Corporation's Objections to the Report and Recommendation Regarding Claim Construction, Doc. 230, *Masimo Corporation v. Philips Electronics North America Corporation and Philips Medizin Systeme Böblingen GMBH*, District of Delaware, Case No. 1:09-cv-00080 (LPS/MPT) dated Mar. 24, 2011.

Masimo Corporation's Objections to the Report and Recommendation Regarding Claim Construction, Doc. 219, *Masimo Corporation v. Philips Electronics North America Corporation and Philips Medizin Systeme Böblingen GMBH*, (District of Delaware, Case No. 1:09-cv-00080 (LPS/MPT) dated Mar. 8, 2011.

Defendant's Objections to Magistrate Judge Thynge's Report and Recommendation Regarding Claim Construction, Doc. 218, *Masimo Corporation v. Philips Electronics North America Corporation and Philips Medizin Systeme Böblingen GMBH*, (District of Delaware Case No. 1:09-cv-00080 (LPS/MPT) dated Mar. 7, 2011.

Report and Recommendation Regarding Claim Construction, Doc. 210, *Masimo Corporation v. Philips Electronics North America Corporation and Philips Medizin Systeme Böblingen GMBH*, (District of Delaware, Case No. 1:09-cv-00080 (LPS/MPT) dated Feb. 18, 2011.

Memorandum Order Adopting Report and Recommendation Regarding Claim Construction, Doc. 319, *Masimo Corporation v. Philips Electronics North America Corporation and Philips*

(56) References Cited

OTHER PUBLICATIONS

*Medizin Systeme Böblingen GMBH*, (District of Delaware, Case No. 1:09-cv-00080 (LPS/MPT) dated Feb. 18, 2011.

Masimo Corporation's Response to Defendant's Objections to the Report and Recommendation Regarding Claim Construction, Doc. 232, *Masimo Corporation v. Philips Electronics North America Corporation and Philips Medizin Systeme Böblingen GMBH*, (District of Delaware, Case No. 1:09-cv-00080 (LPS/MPT) dated Mar. 24, 2011.

V. Ya Volkov, "Principles and Algorithms for Determing Blood Oxygenation Level by Pulse Oximetry," *Biomedical Engineering*, vol. 27, No. 1 (Jan.-Feb. 1993) (translated from Russian).

Supplemental Expert Report of Dr. Robert Stone Regarding the Invalidity of Masimo's Patents-in-Suit (U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated Mar. 18, 2012.

Appendixes for Expert Report of Dr. Robert Stone Regarding the Invalidity of Masimo's Patents-in-Suit (U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated May 7, 2012.

Expert Report of Dr. Robert Stone Regarding the Invalidity of Masimo's Patents-in-Suit(U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated May 7, 2012.

Revised Expert Report of Dr. Robert Stone Regarding the invalidity of Masimo's Patents-in-Suit (U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated May 7, 2012.

Wukitsch, et al., "Knowing Your Monitoring Equipment," *Journal of Clinical Monitoring*, vol. 4, No. 4 (Oct. 1998).

Second Amended Complaint for Patent Infringement, Doc. 42, *Masimo Corporation v. Philips Electronics North America Corporation and Philips Medizin Systeme Böblingen GMBH*, (District of Delaware, Case No. 1:11-cv-00742 (LPS/MPT) dated Apr. 25, 2012.

Masimo's Answer to Philips' Counterclaims, Doc. 28, *Masimo Corporation v. Philips Electronics North America Corporation and Philips Medizin System Böblingen GMBH*, (District of Delaware, Case No. 1:11-cv-00742 (LPS/MPT) dated Dec. 30, 2011.

Defendant's Answer and Philips Electronics North America Corp.'s Counterclaims to Masimo's First Amended Complaint, Doc. 11, *Masimo Corporation v. Philips Electronics North America Corporation and Philips Medizin Systeme Böblingen GMBH*, (District of Delaware, Case No. 1:11-cv-00742 (LPS/MPT) dated Nov. 7, 2011.

Masimo's Answer to Philip's Counterclaims to Masimo's Second Amended Complaint, doc. 358, *Masimo Corporation v. Philips Electronics North America Corporation and Philips Medizin Systeme Böblingen GMBH*, (District of Delaware, Case No. 1:11-cv-00742 (LPS/MPT) dated Jun. 4, 2012.

Defendants' Answer and Philips Electronics North America Corp.'s Counterclaims to Masimo's Second Amended Complaint, Doc. 43, *Masimo Corporation v. Philips Electronics North America Corporation and Philips Medizin Systeme Böblingen GMBH*, (District of Delaware, Case No. 1:11-cv-00742 (LPS/MPT) dated May 11, 2012.

\* cited by examiner

PLETHYSMOGRAPH PULSE RECOGNITION PROCESSOR

CROSS-REFERENCE TO RELATED APPLICATION

The present application claims priority benefit under 35 U.S.C. §120 to, and is a continuation of U.S. patent application Ser. No. 11/418,328, filed May 3, 2006, entitled "Plethysmograph Pulse Recognition Processor," now U.S. Pat. No. 7,988,637, which is a continuation of U.S. patent application Ser. No. 10/974,095, filed Oct. 27, 2004, entitled "Plethysmograph Pulse Recognition Processor," now U.S. Pat. No. 7,044,918, which is a continuation of U.S. patent application Ser. No. 10/267,446, filed Oct. 8, 2002, entitled "Plethysmograph Pulse Recognition Processor," now U.S. Pat. No. 6,816,741, which is a continuation of U.S. patent application Ser. No. 09/471,510, filed Dec. 23, 1999, entitled "Plethysmograph Pulse Recognition Processor," now U.S. Pat. No. 6,463,311, which claims priority benefit under 35 U.S.C. §119(e) from U.S. Provisional Application No. 60/114,127, filed Dec. 30, 1998, entitled "Plethysmograph Pulse Recognition Processor." The present application also incorporates the foregoing utility disclosures herein by reference.

BACKGROUND OF THE INVENTION

Oximetry is the measurement of the oxygen status of blood. Early detection of low blood oxygen is critical in the medical field, for example in critical care and surgical applications, because an insufficient supply of oxygen can result in brain damage and death in a matter of minutes. Pulse oximetry is a widely accepted noninvasive procedure for measuring the oxygen saturation level of arterial blood, an indicator of oxygen supply. A pulse oximeter typically provides a numerical readout of the patient's oxygen saturation, a numerical readout of pulse rate, and an audible indicator or "beep" that occurs at each pulse.

A pulse oximetry system consists of a sensor attached to a patient, a monitor, and a cable connecting the sensor and monitor. Conventionally, a pulse oximetry sensor has both red and infrared (IR) light-emitting diode (LED) emitters and a photodiode detector. The sensor is typically attached to an adult patient's finger or an infant patient's foot. For a finger, the sensor is configured so that the emitters project light through the fingernail and into the blood vessels and capillaries underneath. The photodiode is positioned at the fingertip opposite the fingernail so as to detect the LED emitted light as it emerges from the finger tissues.

The pulse oximetry monitor (pulse oximeter) determines oxygen saturation by computing the differential absorption by arterial blood of the two wavelengths emitted by the sensor. The pulse oximeter alternately activates the sensor LED emitters and reads the resulting current generated by the photodiode detector. This current is proportional to the intensity of the detected light. The pulse oximeter calculates a ratio of detected red and infrared intensities, and an arterial oxygen saturation value is empirically determined based on the ratio obtained. The pulse oximeter contains circuitry for controlling the sensor, processing the sensor signals and displaying the patient's oxygen saturation and pulse rate. In addition, a pulse oximeter may display the patient's plethysmograph waveform, which is a visualization of blood volume change in the illuminated tissue caused by arterial blood flow over time. A pulse oximeter is described in U.S. Pat. No. 5,632,272 assigned to the assignee of the present invention.

SUMMARY OF THE INVENTION

FIG. 1 illustrates the standard plethysmograph waveform 100, which can be derived from a pulse oximeter. The waveform 100 is a display of blood volume, shown along the y-axis 110, over time, shown along the x-axis 120. The shape of the plethysmograph waveform 100 is a function of heart stroke volume, pressure gradient, arterial elasticity and peripheral resistance. The ideal waveform 100 displays a broad peripheral flow curve, with a short, steep inflow phase 130 followed by a 3 to 4 times longer outflow phase 140. The inflow phase 130 is the result of tissue distention by the rapid blood volume inflow during ventricular systole. During the outflow phase 140, blood flow continues into the vascular bed during diastole. The end diastolic baseline 150 indicates the minimum basal tissue perfusion. During the outflow phase 140 is a dicrotic notch 160, the nature of which is disputed. Classically, the dicrotic notch 160 is attributed to closure of the aortic valve at the end of ventricular systole. However, it may also be the result of reflection from the periphery of an initial, fast propagating, pressure pulse that occurs upon the opening of the aortic valve and that precedes the arterial flow wave. A double dicrotic notch can sometimes be observed, although its explanation is obscure, possibly the result of reflections reaching the sensor at different times.

FIG. 2 is a graph 200 illustrating a compartmental model of the absorption of light at a tissue site illuminated by a pulse oximetry sensor. The graph 200 has a y-axis 210 representing the total amount of light absorbed by the tissue site, with time shown along an x-axis 220. The total absorption is represented by layers, including the static absorption layers due to tissue 230, venous blood 240 and a baseline of arterial blood 250. Also shown is a variable absorption layer due to the pulse-added volume of arterial blood 260. The profile 270 of the pulse-added arterial blood 260 is seen as the plethysmograph waveform 100 depicted in FIG. 1.

FIG. 3 illustrates the photo-plethysmograph intensity signal 300 detected by a pulse oximeter sensor. A pulse oximeter does not directly detect absorption and, hence, does not directly measure the standard plethysmograph waveform 100 (FIG. 1). However, the standard plethysmograph can be derived by observing that the detected intensity signal 300 is merely an out of phase version of the absorption profile 270. That is, the peak detected intensity 372 occurs at minimum absorption 272 (FIG. 2), and the minimum detected intensity 374 occurs at maximum absorption 274 (FIG. 2). Further, a rapid rise in absorption 276 (FIG. 2) during the inflow phase of the plethysmograph is reflected in a rapid decline 376 in intensity, and the gradual decline 278 (FIG. 2) in absorption during the outflow phase of the plethysmograph is reflected in a gradual increase 378 in detected intensity.

In addition to blood oxygen saturation, a desired pulse oximetry parameter is the rate at which the heart is beating, i.e. the pulse rate. At first glance, it seems that it is an easy task to determine pulse rate from the red and infrared plethysmograph waveforms described above. However, this task is complicated, even under ideal conditions, by the variety of physiological plethysmographic waveforms. Further, plethysmographic waveforms are often corrupted by noise, including motion artifact, as described in U.S. Pat. No. 2,632,272 cited above. Plethysmograph pulse recognition, especially in the presence of motion artifact and other noise sources, is a useful component for determining pulse rate and also for providing a visual or audible indication of pulse occurrence.

In one aspect of the pulse recognition processor according to the present invention, information regarding pulses within an input plethysmograph waveform is provided at a processor output. The processor has a candidate pulse portion that determines a plurality of potential pulses within the input waveform. A physiological model portion of the processor then determines the physiologically acceptable ones of these potential pulses. The processor may further provide statistics regarding the acceptable pulses. One statistic is pulse density, which is the ratio of the period of acceptable pulses to the duration of an input waveform segment.

The candidate pulse portion has a series of components that remove from consideration as potential pulses those waveform portions that do not correspond to an idealized triangular waveform. This processing removes irrelevant waveform features such as the characteristic dicrotic notch and those caused by noise or motion artifact. The candidate pulse portion provides an output having indices that identify potential pulses relative to the peaks and valleys of this triangular waveform.

The physiological model portion of the processor has a series of components that discard potential pulses that do not compare to a physiologically acceptable pulse. The first component of the model portion extracts features of the potential pulses, including pulse starting point, pulse period, and pulse signal strength. These features are compared against various checks, including checks for pulses that have a period below a predetermined threshold, that are asymmetric, that have a descending trend that is generally slower that a subsequent ascending trend, that do not sufficiently comply with an empirical relationship between pulse rate and pulse signal strength, and that have a signal strength that differs from a short-term average signal strength by greater than a predetermined amount.

In another aspect of the present invention, a pulse recognition method includes the steps of identifying a plurality of potential pulses in an input waveform and comparing the potential pulses to a physiological pulse model to derive at least one physiologically acceptable pulse. A further step of generating statistics for acceptable pulses may also be included. The generating step includes the steps of determining a total period of acceptable pulses and calculating a ratio of this total period to a duration of an input waveform segment to derive a pulse density value. The comparing step includes the steps of extracting pulse features from potential pulses and checking the extracted features against pulse criteria.

Yet another aspect of the current invention is a pulse recognition processor having a candidate pulse means for identifying potential pulses in an input waveform and providing a triangular waveform output. The processor also has a plethysmograph model means for determining physiologically acceptable pulses in the triangular waveform output and providing as a pulse output the indices of acceptable pulses. The pulse recognition processor may further have a pulse statistics means for determining cumulative pulse characteristics from said pulse output.

BRIEF DESCRIPTION OF THE DRAWINGS

The present invention will be described in detail below in connection with the following drawing figures in which.

DETAILED DESCRIPTION OF THE PREFERRED EMBODIMENTS

Figure 4:
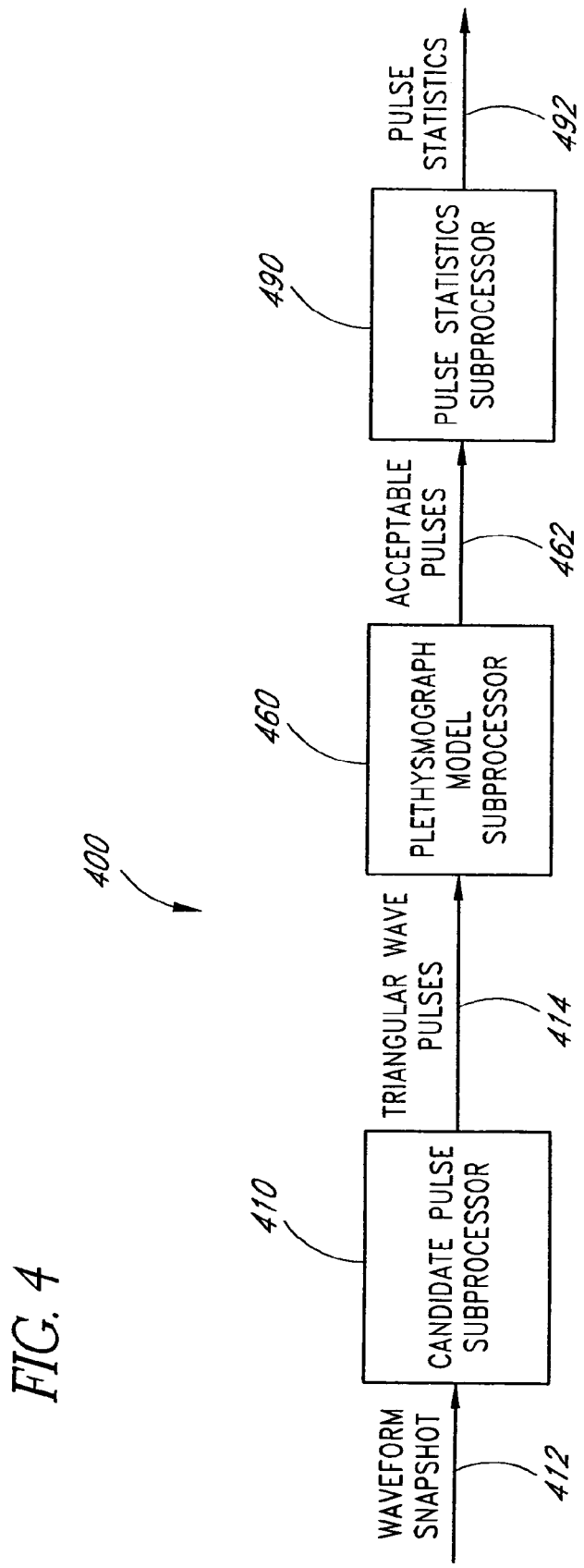
FIG. 4 is a block diagram of the plethysmograph pulse recognition processor according to the present invention.

FIG. 4 illustrates the plethysmograph pulse recognition processor 400 according to the present invention. The pulse processor 400 has three subprocessors, a candidate pulse subprocessor 410, a plethysmograph model subprocessor 460, and a pulse statistics subprocessor 490. The candidate pulse subprocessor 410 applies various waveform criteria or "edge checks" to find candidate pulses in an input waveform "snapshot" 412. In a particular embodiment, the snapshot is 400 samples of a detected intensity plethysmograph taken at a 62.5 Hz sampling rate. This snapshot represents a 6.4 second waveform segment. The output 414 of the candidate pulse subprocessor 410 is peaks and valleys of the input waveform segment representing a triangular wave model of identified candidate pulses. The candidate pulse output 414 is input to the plethysmograph model subprocessor 460, which compares these candidate pulses to an internal model for physiological pulses. The output 462 of the plethysmograph model subprocessor 460 is physiologically acceptable pulses. The acceptable pulse output 462 is input to the pulse statistics subprocessor. The output 492 of the pulse statistics subprocessor is statistics regarding acceptable pulses, including mean pulse period and pulse density, as described below.

Figure 1:
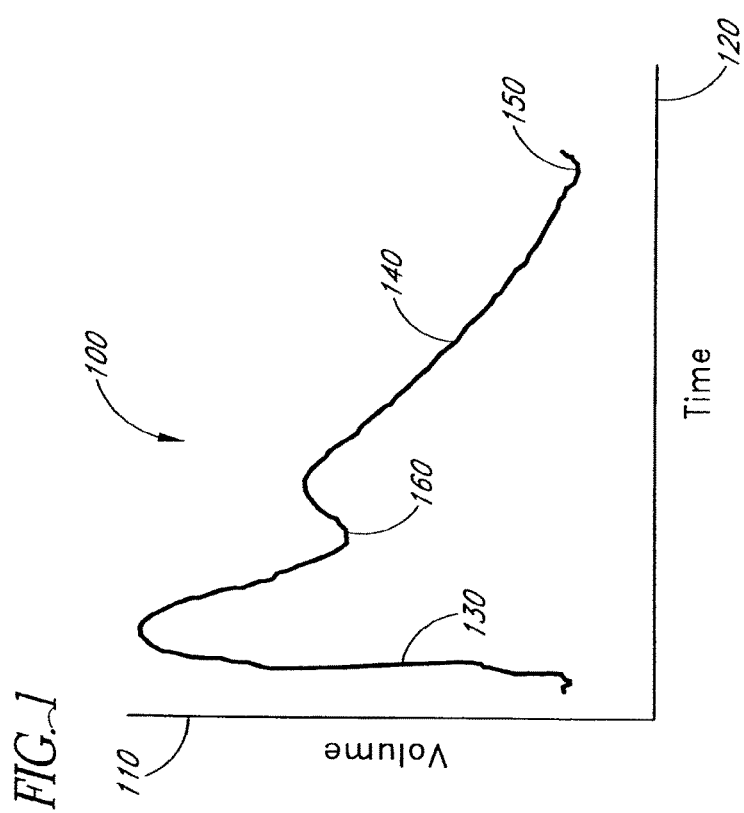
FIG. 1 is a graph illustrating a single pulse of a plethysmograph waveform.
Figure 2:
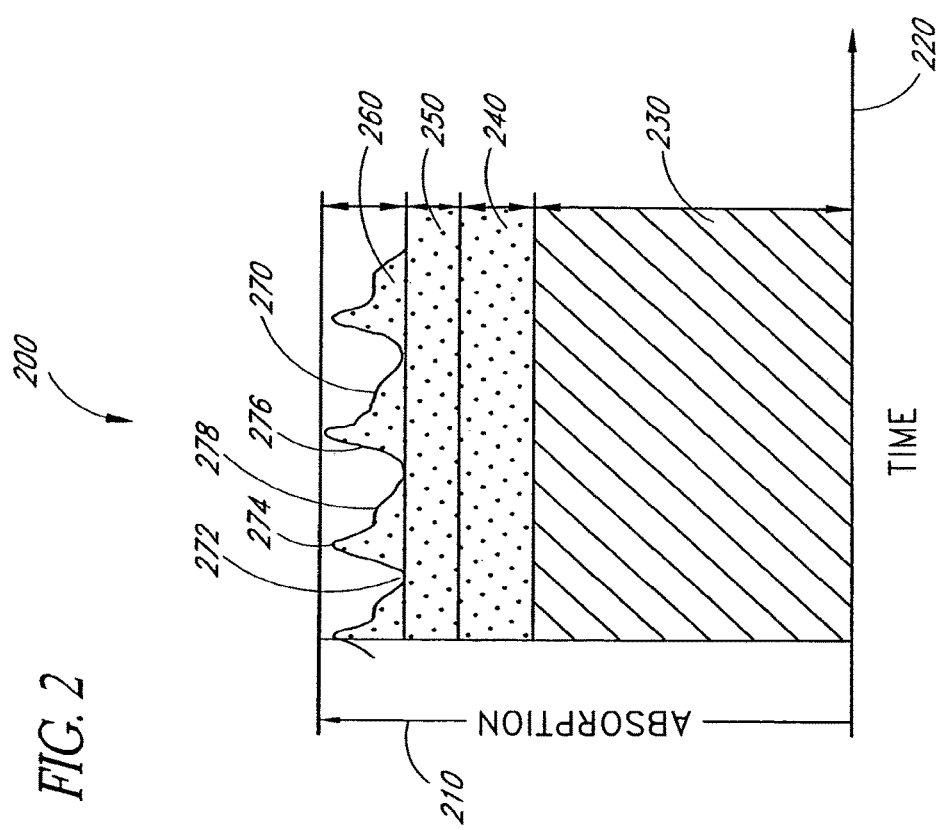
FIG. 2 is a graph illustrating the absorption contribution of various blood and tissue components.
Figure 3:
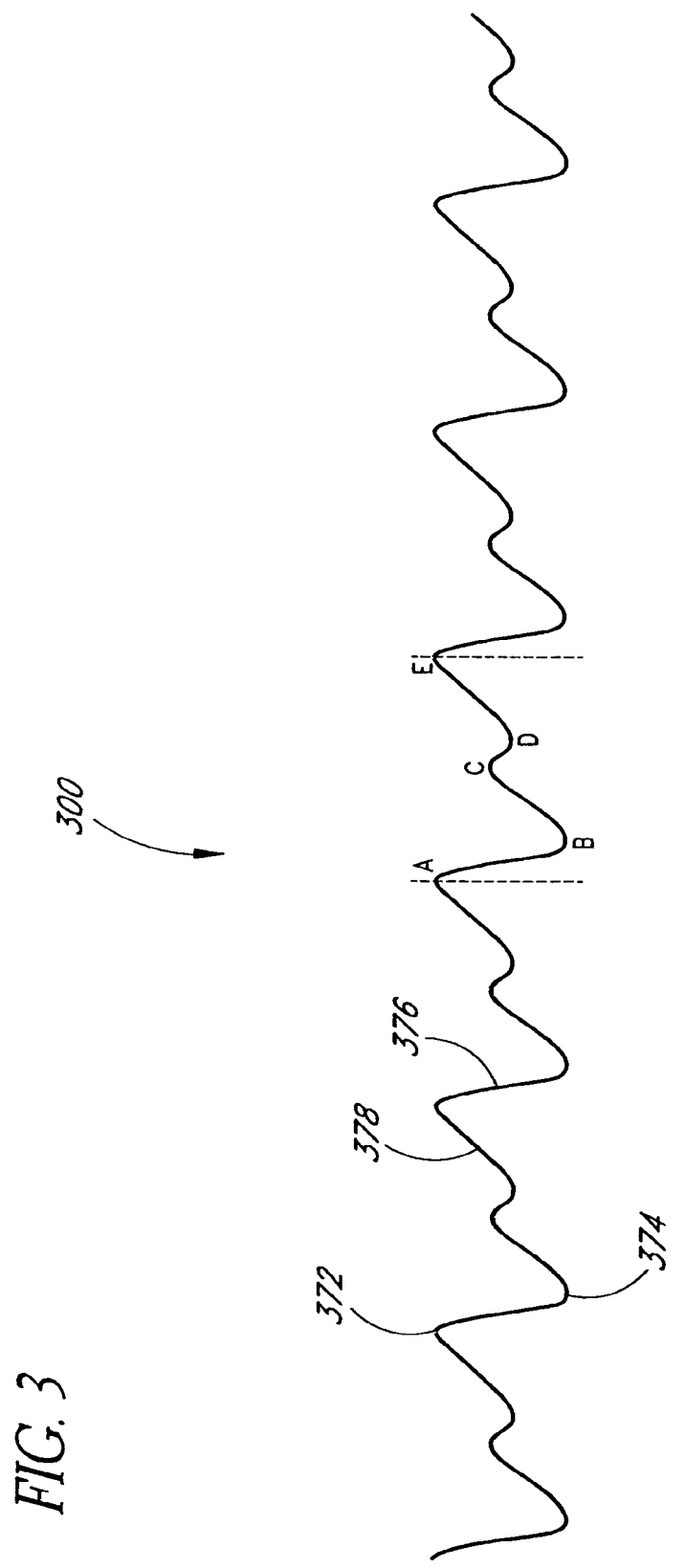
FIG. 3 is a graph illustrating an intensity "plethysmograph" pulse oximetry waveform.
Figure 5:
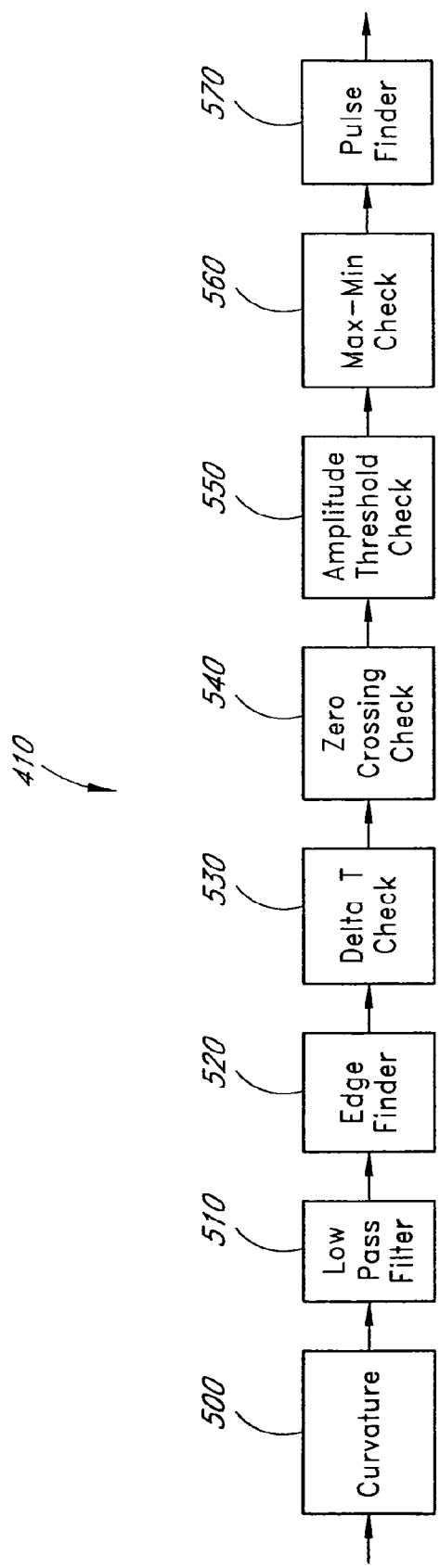
FIG. 5 is a block diagram of the candidate pulse finding subprocessor portion of the present invention.

FIG. 5 illustrates the components of the candidate pulse subprocessor 410. This subprocessor removes waveform features that do not correspond to an idealized triangular waveform, including the characteristic dicrotic notch. For example, as shown in FIG. 3, the candidate pulse component must identify points ABE, discarding points CD. The candidate pulse subprocessor 410 first identifies "edges" within the input waveform segment. An edge is defined as a segment that connects a peak and subsequent valley of the filtered waveform signal. The candidate pulse processor 410 then discards edges that do not meet certain conditions.

As shown in FIG. 5, the candidate pulse subprocessor has curvature 500, low-pass filter 510 (in one embodiment) and edge finder 520 components that identify edges. In one embodiment, the curvature component 510 is implemented by convolving the waveform with the kernel [1,−2, 1]. In one embodiment, instead of a low-pass filter 510, a bandpass filter can be used. For a kernel size of n, this can be represented as follows:

$$y_k = w y_{k-1} + u_k \qquad (1)$$

where $u_k$ is the kth input sample and $y_k$ is the kth output sample and w is a fixed weight that determines the amount of filter feedback. The edge finder 520 identifies the peaks and subsequent valleys of the output of the filter 510.

Figure 6:
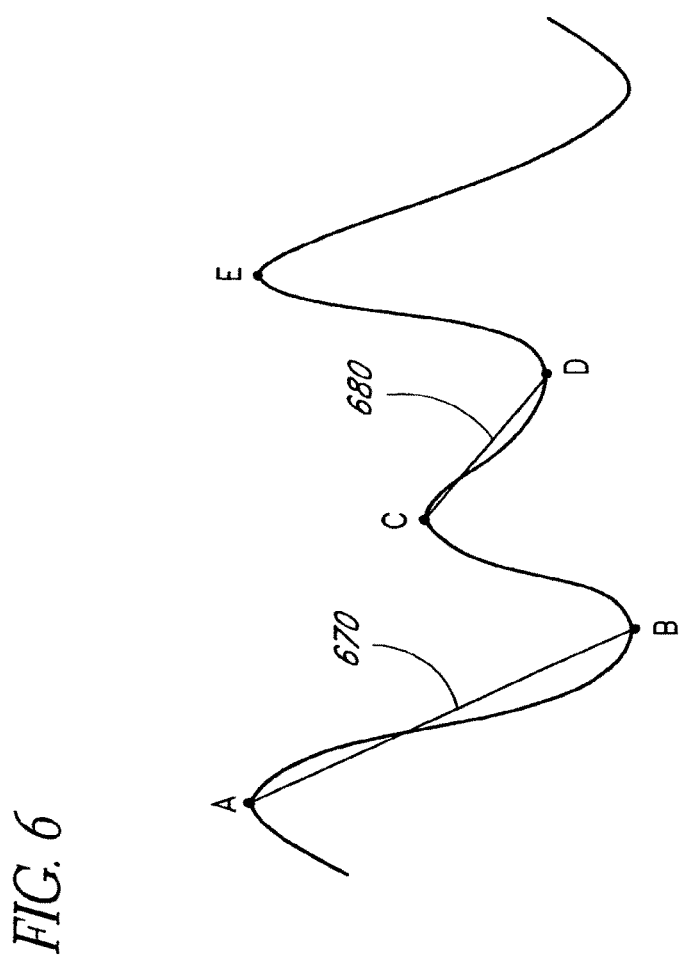
FIG. 6 is a graph illustrating the filtered, curvature of a plethysmograph pulse and the associated edges.

FIG. 6 illustrates the results of the curvature 500, filter 510 and edge finder 520 components applied to a' couple waveform pulses 610. The processed waveform 660 has peaks A and C and corresponding valleys B and D. There are two edges, a first edge is represented by a line segment 670 connecting A and B. A second edge is represented by a line segment 680 connecting C and D.

As shown in FIG. 5, the candidate pulse portion also has delta T 530, zero crossing 540, amplitude threshold 550 and max-min 560 checks that eliminate certain of the identified edges. The delta T check 530 discards all the edges having a distance between end points that do not fall within a fixed interval. This is designed to eliminate pulse-like portions of the input waveform that are either too slow or too quick to be physiological pulses. In a particular embodiment, the interval is between 5 and 30 samples at the 62.5 Hz sampling rate, or 80-480 msec. That is, edges less than 80 msec. or greater than 480 msec. in length are eliminated.

Figure 7:
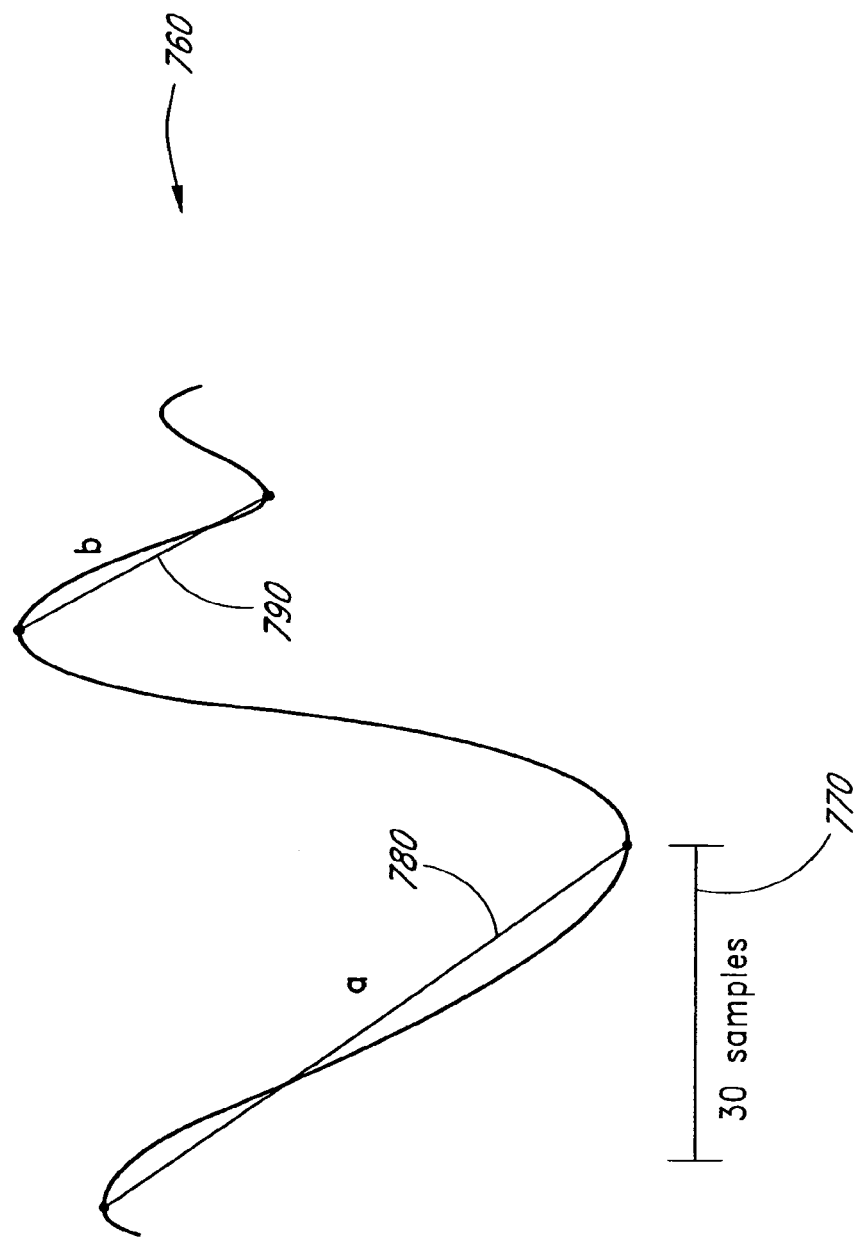
FIG. 7 is a graph illustrating the delta T check on the edges.

FIG. 7 illustrates the delta T check 530 (FIG. 5) described above. Shown is the processed waveform 760, edge a 780 and edge b 790, along with a maximum acceptable edge length interval 770 for comparison. In this example, edge a 780, which is 35 samples in length, would be eliminated as exceeding in length the maximum acceptable interval 770 of 30 samples. By contrast, edge b 790, which is 25 samples in length, would be accepted.

Also shown in FIG. 5, the zero crossing check 540 eliminates all edges that do not cross zero. The zero crossing check eliminates small curvature changes in the input waveform segment, i.e. small bumps that are not peaks and valleys.

Figure 8:
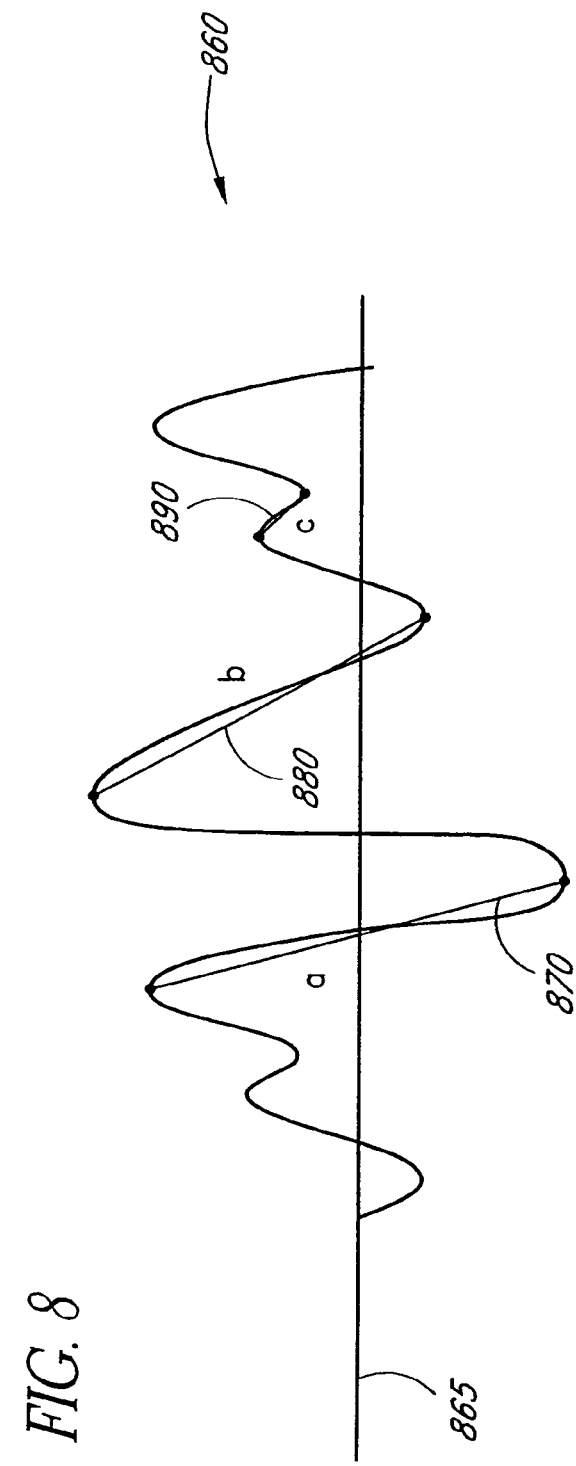
FIG. 8 is a graph illustrating the zero-crossing check on the edges.

FIG. 8 illustrates the effect of the zero crossing check 540 (FIG. 5). Shown is the processed waveform 860. Edge a 870, edge b 880 and edge c 890 are shown relative to the zero line 865 for the processed waveform 860. In this example, edges a 870 and edge b 880 are accepted, but edge c 890 is eliminated because it does not cross the zero line 865.

Shown in FIG. 5, the amplitude threshold check 550 is designed to remove larger "bumps" than the zero crossing check 540, such as dicrotic notches. This is done by comparing the right extreme (valley) of each edge within a fixed-length window to a threshold based on a fixed percentage of the minimum within that window. If the valley is not sufficiently deep, the edge is rejected. In a particular embodiment, the window size is set at 50 samples for neonates and 100 samples for adults in order accommodate the slower pulse rate of an adult. Also, a threshold of 60% of the minimum is used.

Figure 9:
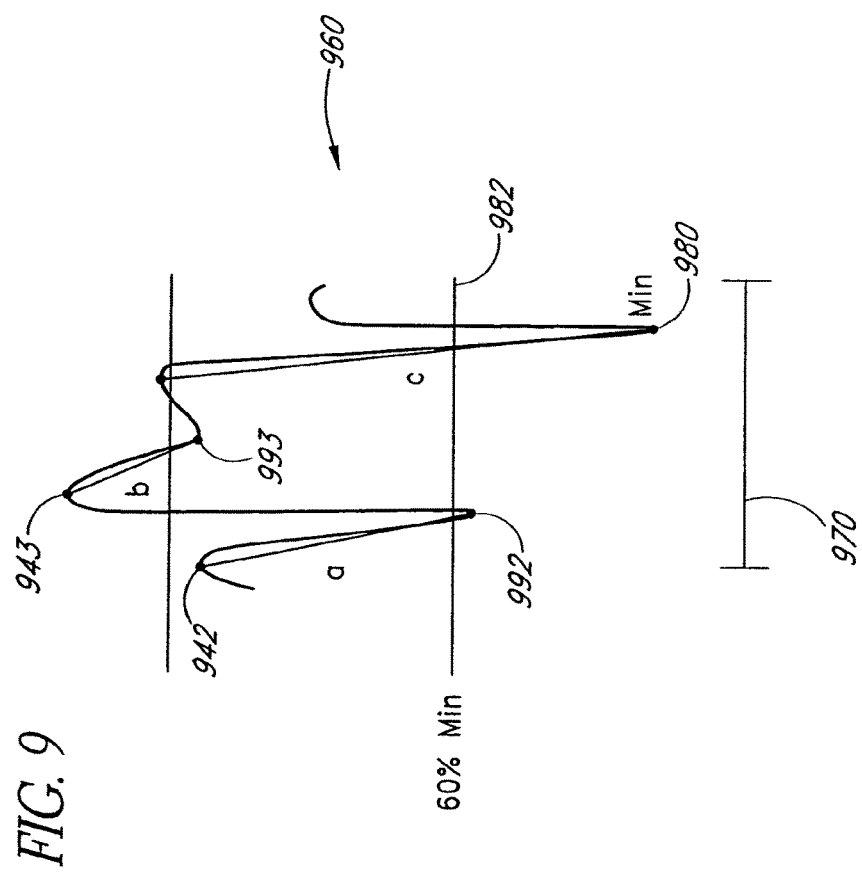
FIG. 9 is a graph illustrating the amplitude threshold check on the edges.

FIG. 9 illustrates an example of the amplitude threshold check 550 (FIG. 5). Shown is a the processed waveform 960. The starting point of the window 970 is set to the left extreme 942 (peak) of the first edge a. A minimum 980 within the window 970 is determined. A threshold 982 equal to 60% of the minimum 980 is determined. The right extreme 992 of edge a is compared with the threshold 982. Edge a is kept because the right extreme 992 is smaller than (more negative) than the threshold 982. The right extreme 993 of edge b is then compared with the threshold 982. Edge b is removed because the right extreme 993 is greater than (less negative) than the threshold 982. Similarly, edge c is kept. Next, the window 970 is moved to the left extreme 943 of edge b and the process repeated.

Also shown in FIG. 5, the max-min check 560 applies another removal criteria to the edges. The max-min check 560 considers the interval of the processed waveform between the minimum of an edge being checked and the peak of the subsequent edge. The max-min check 560 finds the maximum of the processed waveform within this interval. The edge being checked is removed if the maximum is greater than a percentage of the absolute value of the right extreme (minimum) of that edge. In one embodiment requiring the most stringent algorithm performance, the threshold is set to 77% of the right extreme of the edge. In another embodiment with less stringent algorithm performance, the threshold is set to 200% of the right extreme of the edge. The max-min check 560 is effective in eliminating edges that are pulse-like but correspond to motion.

Figure 10:
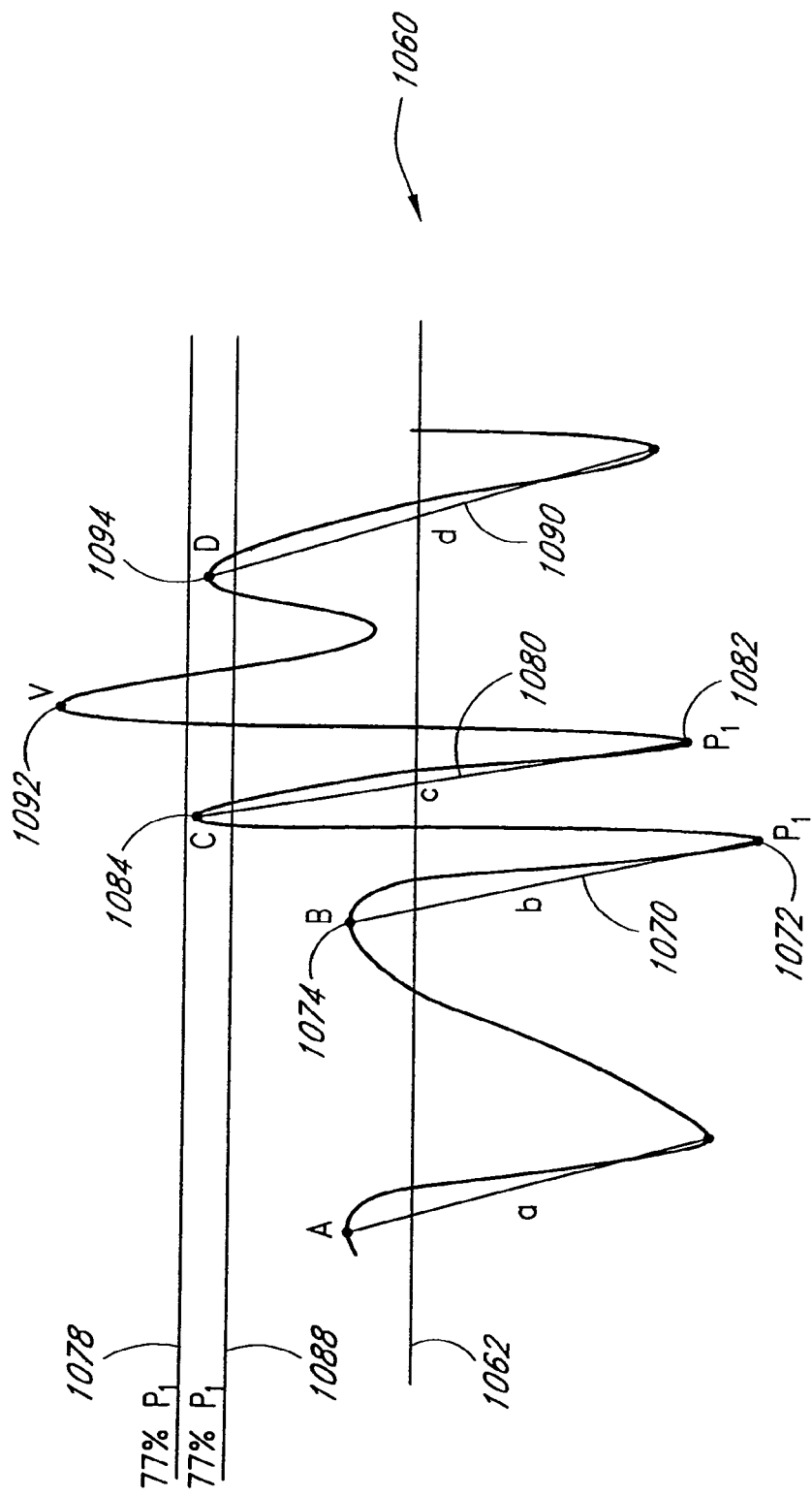
FIG. 10 is a graph illustrating the max-min check on the edges.

FIG. 10 illustrates an example of the max-min check 560 (FIG. 5). Shown is the processed waveform 1060. The max-min check 560 is applied to edge b 1070. The interval B-C is considered, which is between point B 1074, the peak of edge b 1070, and point C 1084, the peak of edge c 1080. The maximum in the interval B-C is point C 1084. Point C 1084 is compared to a first threshold 1078, which in this example is 77% of the absolute value of point P1 1072, the minimum of edge b 1070. Edge b 1070 would not be discarded because point C 1084 is smaller than this first threshold 1078. As another example, the max-min check 560 is applied to edge c 1080. The interval C-D is considered, which is between point C 1084, the peak of edge c 1080, and point D 1094, the peak of edge d 1090. The maximum in the interval C-D is point V 1093. Point V 1093 is compared to a second threshold 1088, which is 77% of the absolute value of point P2 1082, the valley of edge c 1080. Edge c would be discarded because point V 1093 is greater than this second threshold 1088.

As shown in FIG. 5, the pulse finder 570 is the last component of the candidate pulse subprocessor 410. The pulse finder 570 transforms the edges remaining after the various edge checks into candidate pulses in the form of an idealized triangular wave, which are fed into the plethysmograph model subprocessor 460 (FIG. 4). From the information about the indices of the peaks of valleys of the remaining edges, it is simple to determine a pulse in the input waveform. The remaining edges are first divided into edge pairs, i.e. the first and second edges, the second and third edges, and so on. The first point of a pulse corresponds to the maximum of the waveform segment in the interval of indices determined by the peak and valley of the first edge of a pair. The second point is the minimum between the valley of the first edge and the peak of the second edge. The third and last point is the maximum between the peak and the valley of the second edge.

Figure 11:
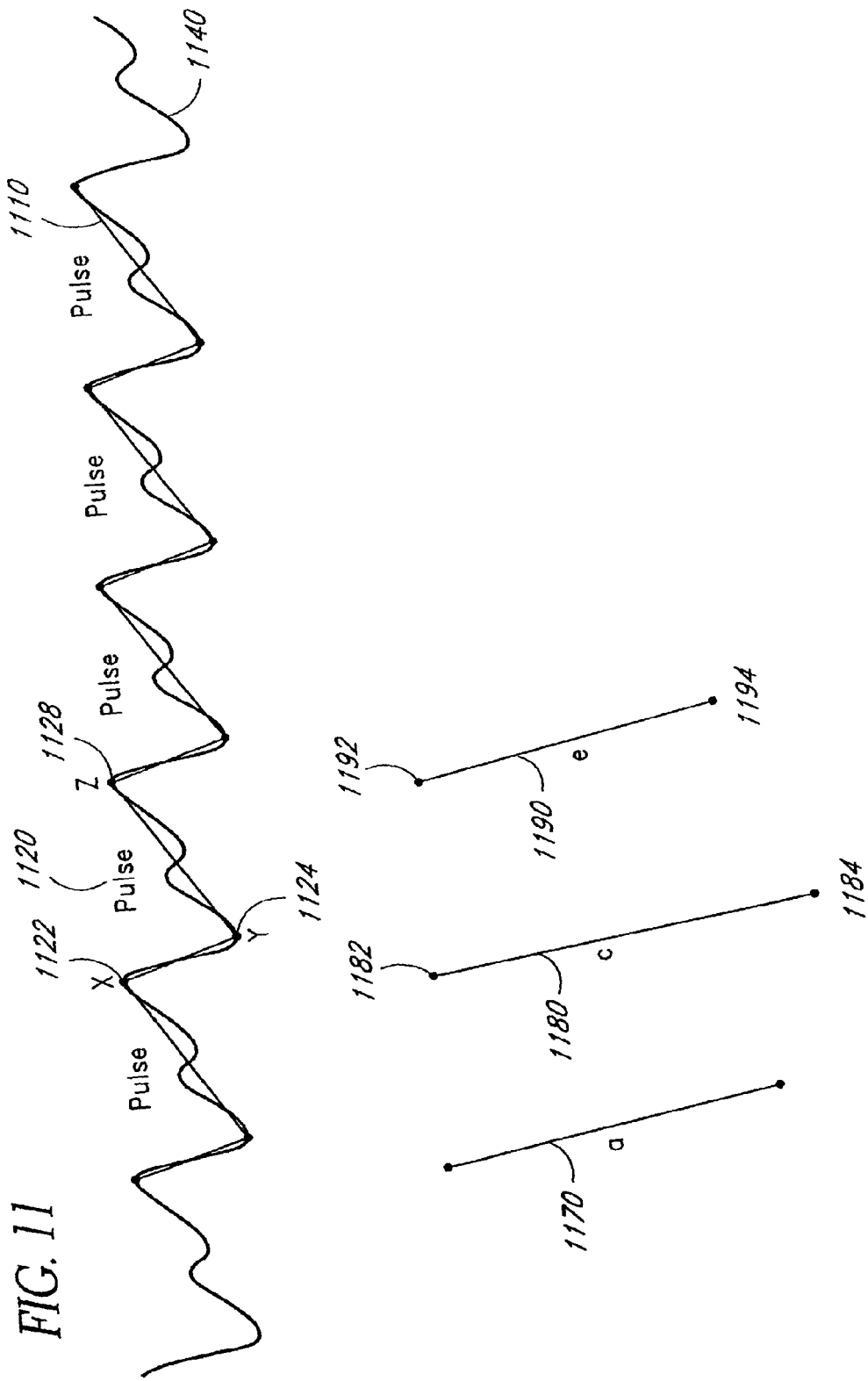
FIG. 11 is a graph illustrating the output of the pulse finder.

FIG. 11 illustrates the result of the pulse finder 570 (FIG. 5) shown as a series of pulses 1110, including a particular pulse XYZ 1120 appearing as a triangular wave superimposed on an input waveform segment 1140. Also shown are the remaining edges a 1170, b 1180 and c 1190. In this example, pulse XYZ 1120 is formed from the pair of edges c 1180 and e 1190. Point X 1122 is the maximum in the waveform segment 1140 in the time interval between the peak 1182 and valley 1184 of edge c 1180. Point Y 1124 is the minimum in the waveform segment 1140 in the time interval between the valley 1184 of edge c 1180 and the peak 1192 of edge e 1190. Point Z 1128 is the maximum in the waveform segment 1140 in the time interval between the peak 1192 and valley 1194 of edge e 1190.

Figure 12:
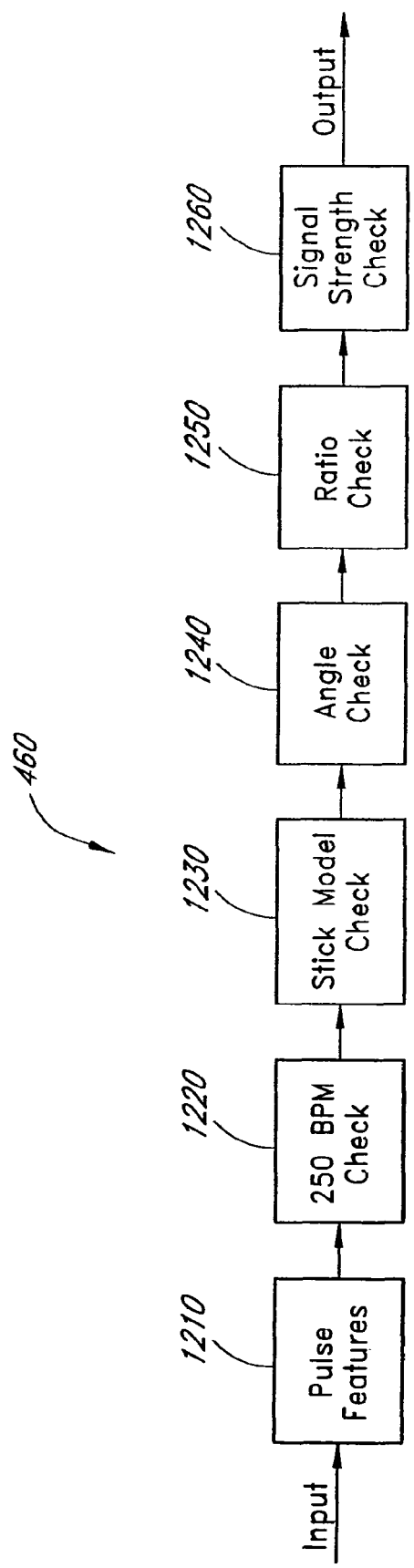
FIG. 12 is a block diagram of the plethysmograph model subprocessor portion of the present invention.

FIG. 12 illustrates the components of the plethysmograph model subprocessor 460. This subprocessor takes as input the candidate pulses identified by the candidate pulse subprocessor 410 (FIG. 4) and decides which of these satisfies an internal model for a physiological plethysmographic waveform. Although the candidate pulse subprocessor 410 (FIG. 4) performs a series of checks on edges, the plethysmograph model subprocessor performs a series of checks on pulse features. The first component of the model subprocessor calculates relevant pulse features. The remainder of the model subprocessor checks these pulse features to identify physiologically acceptable features.

Shown in FIG. 12, the pulse features component 1210 extracts three items of information about the input candidate pulses that are needed for downstream processing by the other components of the model subprocessor. The extracted features are the pulse starting point, period and signal strength.

Figure 13:
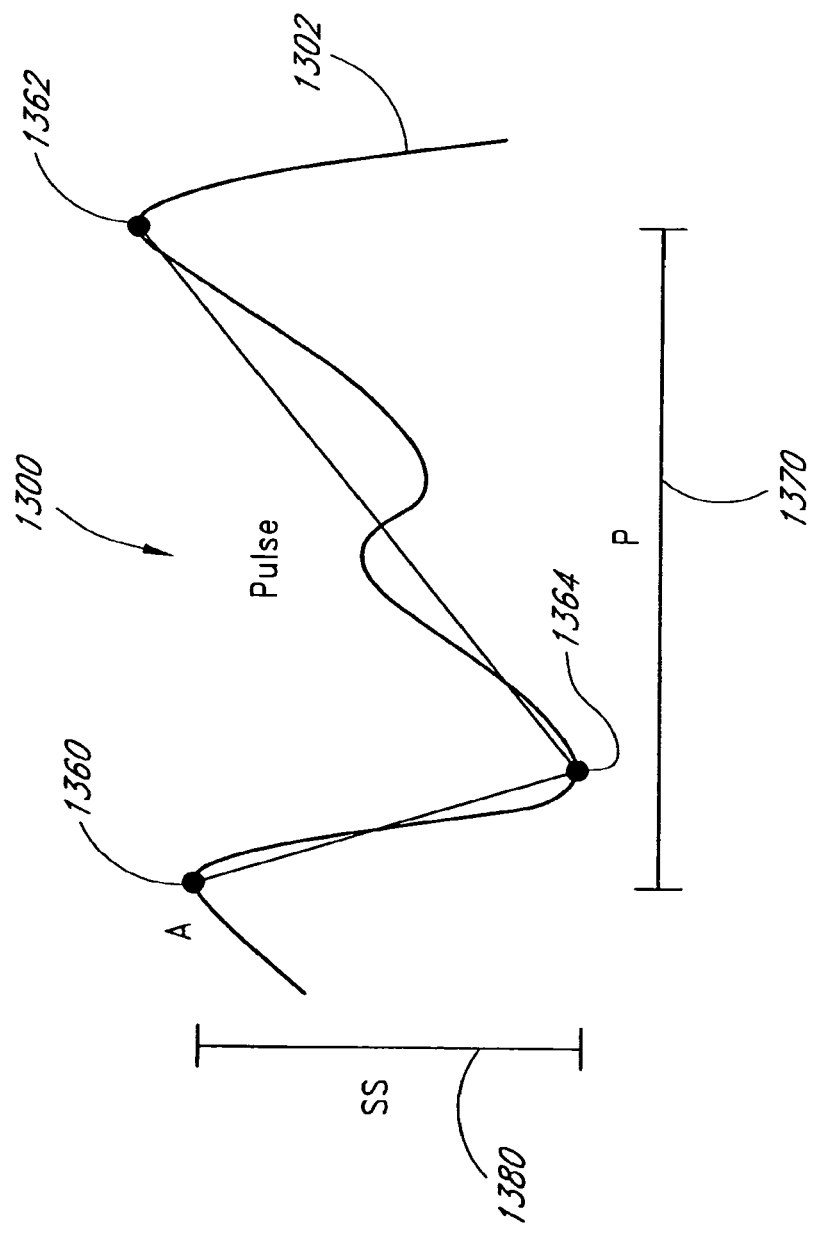
FIG. 13 is a graph illustrating the parameters extracted by the pulse features component of the model subprocessor.

FIG. 13 illustrates a candidate pulse 1300 and the three parameters extracted by the pulse features component 1210 (FIG. 12). The pulse 1300 is shown overlaid on the input waveform 1302 for reference. The starting point A 1360 is the first peak of the pulse 1300. The period P 1370 is the time difference between the time of occurrence of the first peak 1360 and the second peak 1362 of the pulse 1300. The signal strength SS 1350 is the difference between the values of the first peak 1360 and the valley 1364 of the pulse 1300. The signal strength SS 1350 is normalized by dividing this value by the value of the infrared raw signal data at the point corresponding to point A 1360.

Also shown in FIG. 12 is the 250 BPM check 1220. This component discards pulses having a period P 1370 (FIG. 13) that is below 15 samples. This corresponds to an upper limit for the pulse rate set at 250 beats per minute. That is:

$$15 \text{ samples/beat} = (62.5 \text{ samples/sec.} \times 60 \text{ sec./min.})/250 \text{ beats per min} \quad (2)$$

In addition, FIG. 12 shows the stick model check 1230. This component discards pulses where the corresponding waveform does not closely fit a stick model, i.e. where a pulse cannot be represented by a triangular waveform. This component measures a normalized difference between the input waveform and the triangular wave representation of that waveform. The obtained value is compared to a threshold, and pulses are discarded where the normalized difference is greater than that threshold.

Figure 14:
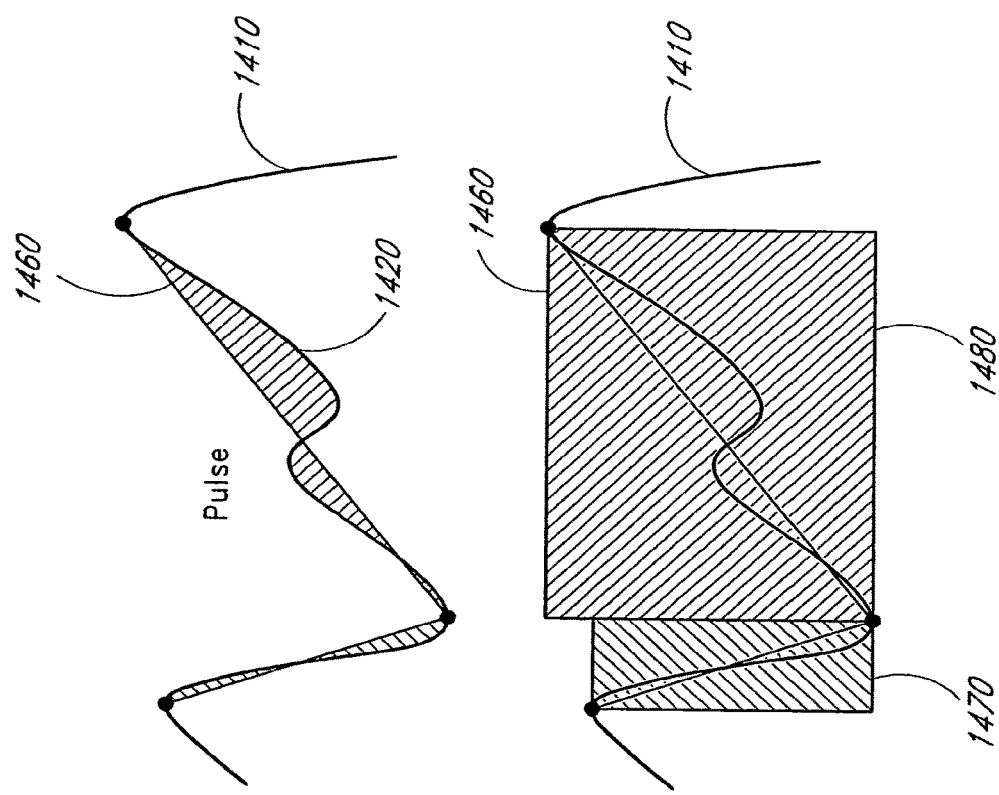
FIG. 14 is a graph illustrating the stick model check on the candidate pulses.

FIG. 14 illustrates the calculations performed by the stick model check 1230 (FIG. 12). Shown is an input waveform pulse 1410 and the corresponding stick model pulse 1460. The stick model check 1230 (FIG. 12) component computes a first value, which is a sum of the absolute differences, shown as the dark black areas 1420, between the waveform pulse 1410 and the stick model pulse 1460. This component also computes a second value, which is a sum of the first rectangular gray area 1470 enclosing the descending portion of the pulse 1410 and the second gray area 1480 enclosing the ascending portion of the pulse 1410. The stick model check 1230 (FIG. 12) then normalizes the first value by dividing it by the second value. This normalized value is compared with a threshold. A physiological pulse does not differ too much from the stick model at high pulse rates. This is not true at pulse rates much below 150 bpm because of the appearance of a dicrotic notch and other "bumps." Hence, the threshold is a function of pulse rate. In one embodiment, the threshold is:

$$0.15, \text{ for pulse rate} < 130 \quad (3)$$

$$0.430455769 e^{-0.008109302}(\text{pulse rate}), \text{ for } 130 < \text{pulse rate} < 160 \quad (4)$$

$$0.1, \text{ for pulse rate} > 160 \quad (5)$$

Shown in FIG. 12 is the angle check 1240. The angle check 1240 is based on computing the angle of a normalized slope for the ascending portion of a pulse. This angle is compared with the same angle of an ideal pulse having the same period. This check is effective in discarding pulses that are extremely asymmetric.

Figure 15:
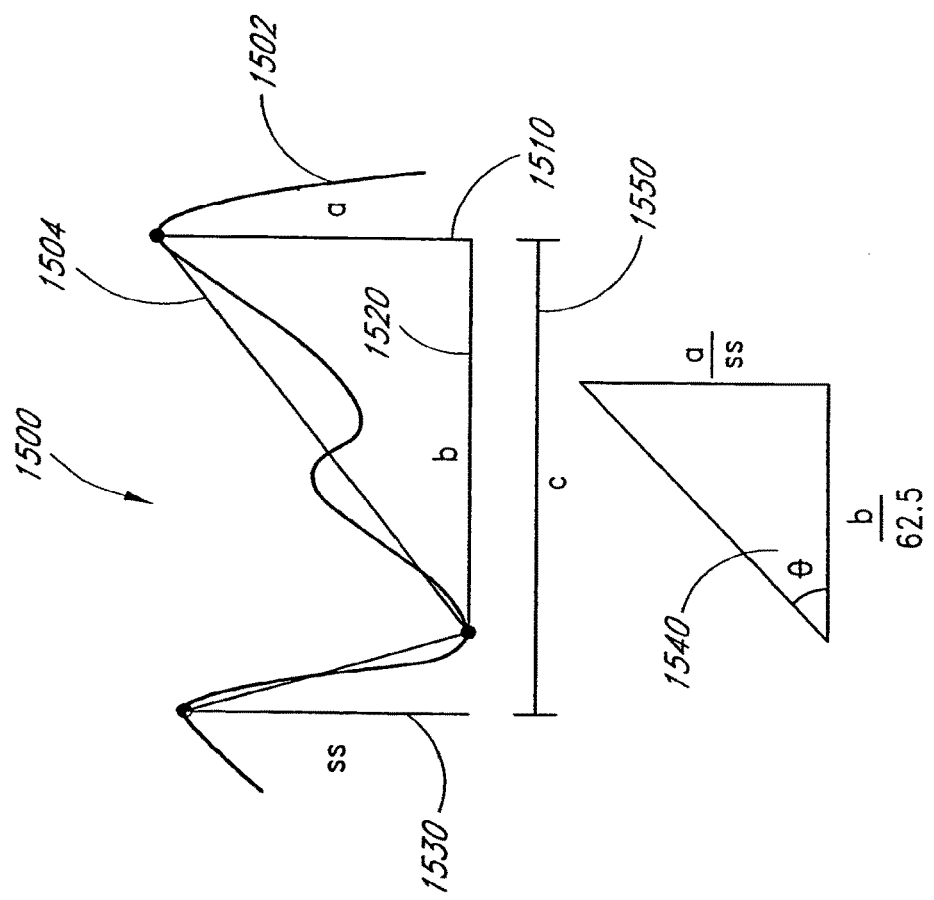
FIG. 15 is a graph illustrating an angle check on the candidate pulses.

FIG. 15 illustrates an example of the angle check 1240 (FIG. 12). Shown is a single triangular pulse 1500 superimposed on the corresponding input waveform 1502. The ascending pulse portion 1504 has a vertical rise a 1510 and a horizontal run b 1520. The rise 1510 and run 1520 are normalized with respect to the pulse signal strength ss 1530 and the pulse frequency, which is 62.5 Hz. in this particular embodiment. An angle θ 1540 is computed as:

$$\theta = \arctan\left[(a/ss)/(b/62.5)\right] \times 180/\pi \quad (6)$$

The angle θ is compared with the same angle of an ideal pulse having the same period, where a is equal to the signal strength and b is equal to the period c 1550 minus 6. Three degrees are added to this value as a threshold margin. Hence, θ is compared to $\theta_{ref}$ computed as follow:

$$\theta_{ref} = \arctan\left\{[a/ss]/[(c-6)/62.5]\right\} \times (180/\pi) + 3 \quad (7)$$

Figure 16:
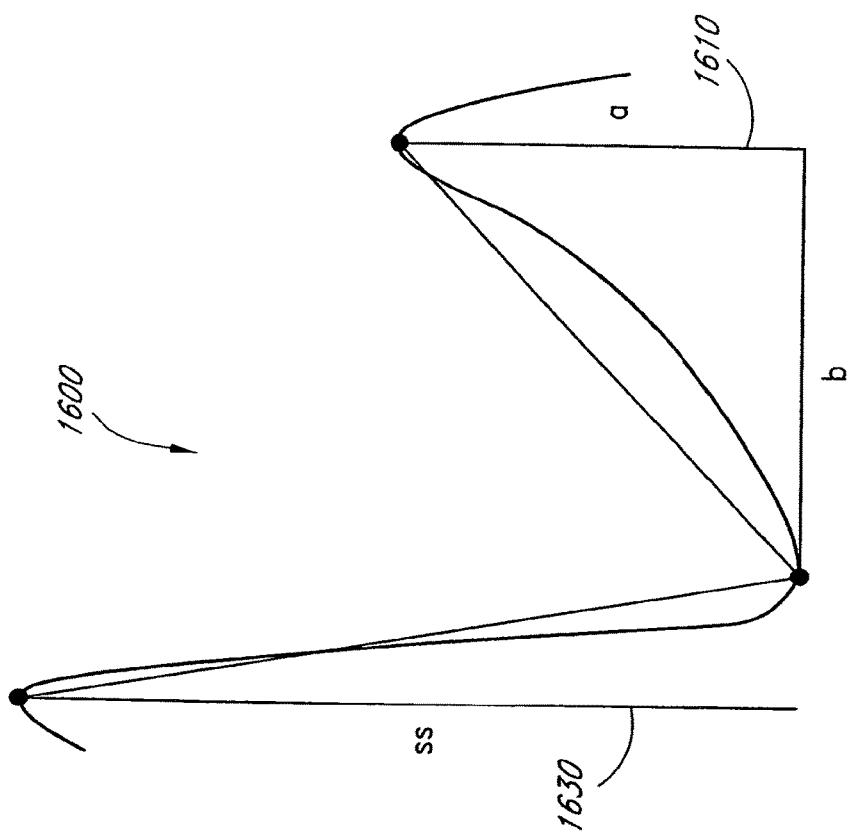
FIG. 16 is a graph illustrating a pulse that would be discarded by the angle check.

If $\theta < \theta_{ref}$, then the pulse is discarded. FIG. 16 illustrates an example pulse 1600 that would be discarded by the angle check, because the segment a 1610 is much smaller than the signal strength ss 1630.

Also shown in FIG. 12 is the ratio check 1250. The time ratio check component removes pulses in which the ratio between the duration of the ascending pulse portion and the duration of the descending pulse portion is less than a certain threshold. In a particular embodiment, the threshold is 1.1. The rationale for this check is that in every physiological pulse the ascending portion is shorter in time than the descending portion, which represents the ventricular contraction.

Figure 17:
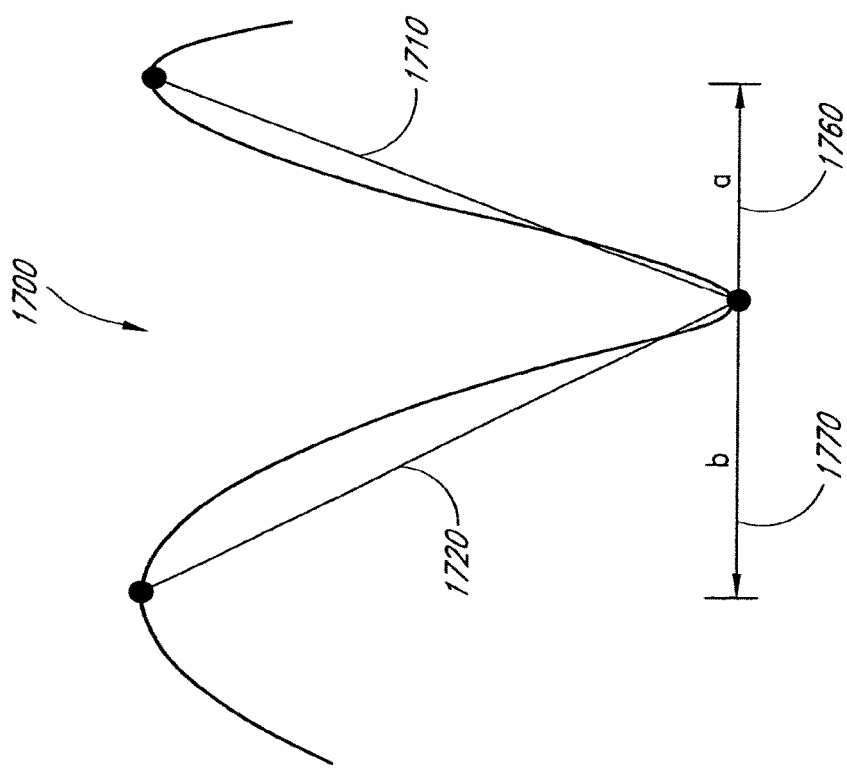
FIG. 17 is a graph illustrating a pulse that would be discarded by the ratio check.

FIG. 17 illustrates an example pulse 1700 that would be discarded by the time ratio check 1250 (FIG. 12). In this example, the duration a 1760 of the ascending portion 1710 is less than the duration b 1770 of the descending portion 1720. Hence, the ratio of the ascending duration 1760 to the descending duration 1770, a/b, is less than the threshold 1.1.

FIG. 12 further shows the signal strength check 1260. The signal strength check 1260 assigns a confidence value to each pulse, based on its signal strength. There are two levels of confidence, high and low. The determination of confidence is based on two mechanisms. The first mechanism is founded on the observation that the higher the pulse rate, the lower the signal strength. This mechanism is implemented with an empirical relationship between pulse rate and signal strength. If the measured signal strength is greater than this empirical relationship by a fixed margin, the pulse confidence is low. The second mechanism incorporates the physiological limitation that signal strength cannot change too much over a short period of time. If the pulse signal strength is greater than a short-term average signal strength by a fixed margin, the pulse confidence is low. If the pulse meets both criteria, then the pulse has a high confidence. All pulses in a single waveform segment or snapshot have the same confidence value. Hence, if there is a least one pulse with a high confidence, then all pulses with a low confidence will be dropped.

Figure 18:
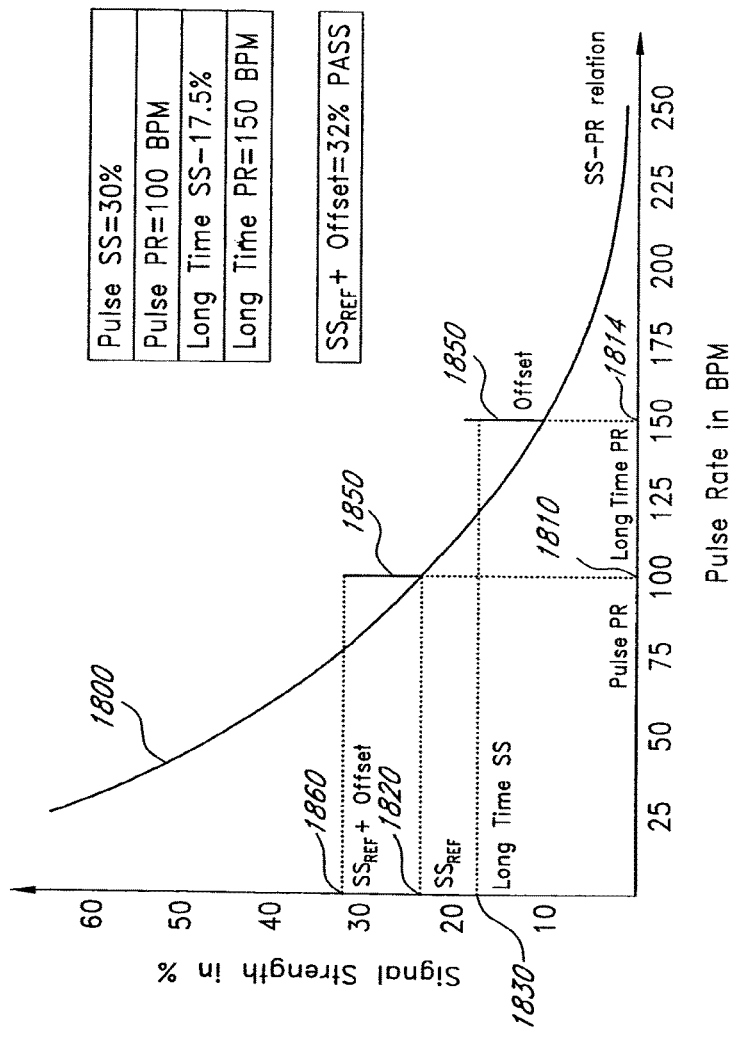
FIG. 18 is a graph illustrating one test of the signal strength check.

FIG. 18 illustrates the first signal strength criteria described above. In one embodiment, the relationship between signal strength and pulse rate is given by curve 1800, which is described by the following equation:

$$SS = 110 \cdot e^{-0.02131 PR} + 1 \qquad (8)$$

First, the pulse rate, PR 1810, is determined from the pulse period. Next, the corresponding signal strength, $SS_{ref}$ 1820, is determined from equation (8) and the pulse rate 1810. Because equation (8) is empirically derived, it is shifted up and down to make it more applicable for individual patients. A long-term average signal strength, Long Time SS 1830, and a long-term average pulse rate, Long Time PR 1840, are derived. If Long Time SS 1830 is above the curve 1800 at the point corresponding to the Long Time PR 1840, then the difference between the Long Time SS and the curve 1800 plus 2 becomes Offset 1850. If the measured pulse signal strength, Pulse SS, is less than $SS_{ref}$+Offset 1860, then this check is passed.

As shown in FIG. 4, after the candidate pulse subprocessor 410 and the plethysmograph model subprocessor 460, the pulse recognition processor 400 has identified inside the input waveform snapshot all of the pulses that meet a certain model for physiologically acceptable plethysmographs. From the information about these pulses, the pulse statistics subprocessor 490 can extract statistics regarding the snapshot itself. Two useful statistical parameters that are derived are the median value of the pulse periods and signal strengths. The median is used rather than the mean because inside a waveform snapshot of 400 points (almost 7 seconds) the period and signal strength associated with each pulse can vary widely. Another parameter is the signal strength confidence level, which in one embodiment is the same for all the recognized pulses of a snapshot. A fourth useful parameter is pulse density. Pulse density is the value obtained by dividing the sum of the periods of the acceptable pulses by the length of the snapshot. Pulse density represents that ratio of the snapshot that has been classified as physiologically acceptable. Pulse density is a value between 0 and 1, where 1 means that all of the snapshot is physiologically acceptable. In other words, pulse density is a measure of whether the data is clean or distorted, for example by motion artifact.

Figure 19:
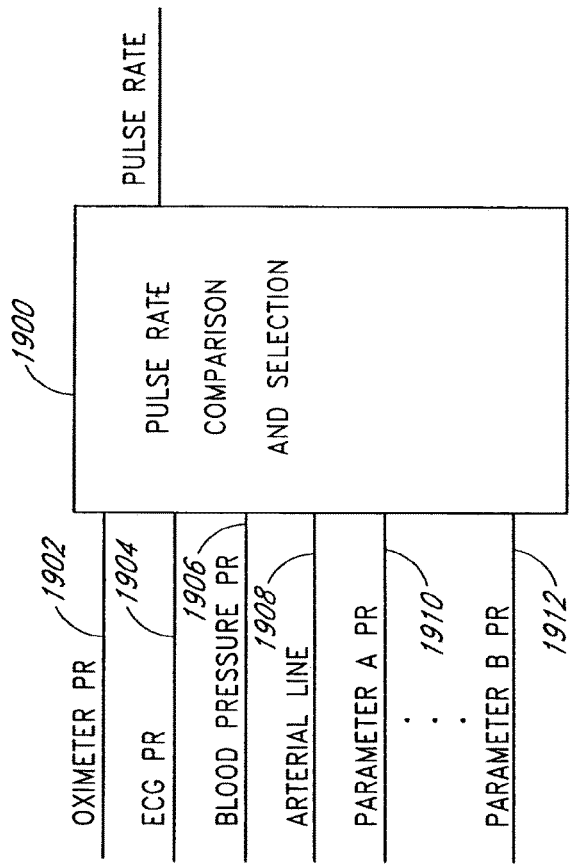
FIG. 19 is a block diagram of a pulse rate selection and comparison module in accordance with a preferred embodiment of the present invention.

Finally, based on these described criteria, a pulse rate may be chosen. In a system with additional monitoring inputs, as depicted in FIG. 19, a pulse rate selection and comparison module 1900 may be provided. For example, the oximeter pulse rate (and corresponding confidence information if desired) can be provided on a first input 1902. In a multi-parameter patient monitor, there may also be pulse rate or pulse information (and possibly confidence information) from an ECG or EKG monitor on a second input 1904, from a blood pressure monitor on a third input 1906, from an arterial line on a fourth input 1908, and other possible parameters 1910, 1912. The pulse rate module 1900 then compares the various inputs, and can determine which correlate or which correlate and have the highest confidence association. The selected pulse rate is then provided on an output 1914. Alternatively, the pulse rate module 1900 may average each input, a selection of the inputs or provide a weighted average based on confidence information if available.

The plethysmograph pulse recognition processor has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. A method of determining a pulse rate measurement of a monitored patient from a signal responsive to light absorption by tissue of the monitored patient, said method comprising:
    receiving data from a plurality of sensors including a noninvasive optical sensor, wherein said data is responsive to light attenuated by tissue;
    electronically processing said data using an electronic signal processor including:
        identifying candidate pulses from the received data based on a triangular wave model;
        extracting pulse features from the identified candidate pulses;
        determining physiologically acceptable pulses from the identified candidate pulses based on the extracted pulse features;
        extracting one or more pulse statistics from the determined physiologically acceptable pulses, wherein said one or more pulse statistics represent a confidence associated with the physiologically acceptable pulses;
        selecting a pulse rate from pulse measurements derived from the plurality of sensors based on the extracted one or more pulse statistics representing the confidence associated with the physiologically acceptable pulses; and
        displaying the selected pulse rate,
        wherein said one or more pulse statistics comprise pulse density.

2. The method of claim 1, wherein said pulse statistics comprise at least one of median value of pulse periods, signal strength of pulses, and signal strength confidence level.

3. A system for determining a rate measurement of a monitored patient from a signal responsive to light absorption by tissue of a monitored patient, said system comprising an electronic signal processor configured to:
    receive data from a plurality of sensors including a noninvasive optical sensor, wherein said data is responsive to light attenuated by tissue, wherein said tissue may vary in optical density over time due to volumetric changes;
    identify candidate pulses from the received data based on a triangular wave model;
    extract pulse features from the identified candidate pulses;
    determine physiologically acceptable pulses from the identified candidate pulses based on the extracted pulse features;

calculate one or more pulse statistics of the determined physiologically acceptable pulses;
select a pulse rate from pulse measurements derived from the plurality of sensors based on the calculated one or more pulse statistics of the determined physiologically acceptable pulses; and
display the selected pulse rate,
wherein the one or more pulse statistics comprise pulse density.

4. The system of claim 3, wherein the pulse features comprise at least one of the following: pulse starting point, period, and signal strength.

\* \* \* \* \*

UNITED STATES PATENT AND TRADEMARK OFFICE
CERTIFICATE OF CORRECTION

PATENT NO. : 9,675,286 B2  
APPLICATION NO. : 13/196220  
DATED : June 13, 2017  
INVENTOR(S) : Mohamed K. Diab Page 1 of 1

It is certified that error appears in the above-identified patent and that said Letters Patent is hereby corrected as shown below:

On the Title Page

In Column 1 (page 7, item (56)) at Line 4, Under Other Publications, change "of of" to --of--.

In Column 2 (page 7, item (56)) at Line 9, Under Other Publications, change "90/002,183," to --95/002,183,--.

In Column 2 (page 7, item (56)) at Line 18, Under Other Publications, change "aligner" to --Wigner--.

In Column 1 (page 9, item (56)) at Line 11, Under Other Publications, change "Determing" to --Determining--.

In the Specification

In Column 5 at Line 27, Change "a'" to --a--.

In Column 6 at Line 8, Change "a the" to --the--.

In Column 8 at Lines 37-38 (approx.), Change "$\theta=\arctan[(a/ss)/(b/62.5)]\times 180/\pi$" to --$\theta=\arctan[(a/ss)/(b/62.5)]\times 180/\pi$--.

In Column 8 at Lines 44-45 (approx.), Change "$\theta_{ref}=\arctan\{[a/ss]/[(c-6)/62.5]\} \times (180/\pi)+3$" to --$\theta_{ref}=\arctan\{[a/ss]/[(c-6)/62.5]\}\times(180/\pi)+3$--.

In the Claims

In Column 10 at Line 53, In Claim 3, after "a" insert --pulse--.

Signed and Sealed this  
Seventeenth Day of October, 2017

Joseph Matal  
*Performing the Functions and Duties of the*  
*Under Secretary of Commerce for Intellectual Property and*  
*Director of the United States Patent and Trademark Office*